US009808591B2

United States Patent
Esmaeil-zadeh-azar

(10) Patent No.: US 9,808,591 B2
(45) Date of Patent: Nov. 7, 2017

(54) METHODS AND SYSTEMS FOR BREATH DELIVERY SYNCHRONIZATION

(71) Applicant: COVIDIEN LP, Boulder, CO (US)

(72) Inventor: Farhad Esmaeil-zadeh-azar, Vista, CA (US)

(73) Assignee: COVIDIEN LP, Mansfield, CO (US)

( * ) Notice: Subject to any disclaimer, the term of this patent is extended or adjusted under 35 U.S.C. 154(b) by 503 days.

(21) Appl. No.: 14/460,615

(22) Filed: Aug. 15, 2014

(65) Prior Publication Data

US 2016/0045694 A1 Feb. 18, 2016

(51) Int. Cl.
*A61M 16/00* (2006.01)
*A61B 5/00* (2006.01)
(Continued)

(52) U.S. Cl.
CPC ........... *A61M 16/0069* (2014.02); *A61B 5/08* (2013.01); *A61B 5/4538* (2013.01);
(Continued)

(58) Field of Classification Search
CPC ....... A61B 5/08; A61B 5/113; A61B 5/14552; A61B 5/4538; A61B 5/4836; A61B 5/6844; A61B 5/7203; A61B 5/7221; A61B 5/7239; A61B 5/7246; A61B 5/7278; A61B 5/7289; A61M 16/00; A61M 16/0051; A61M 16/0069; A61M 16/0677; A61M 2016/0021; A61M 2016/0027; A61M 2016/003; A61M 2016/0039; A61M 2016/0042; A61M 2202/03; A61M 2205/3303; A61M 2205/502; A61M 2205/8225; A61M 2230/40
(Continued)

(56) References Cited

U.S. PATENT DOCUMENTS 3,575,167 A 4/1971 Michielsen
3,584,621 A 6/1971 Bird et al.
(Continued)

FOREIGN PATENT DOCUMENTS

EP 521515 1/1993
EP 1005829 6/2000
(Continued)

OTHER PUBLICATIONS

Malladi, D.P. et al., "A generalized Shiryayev sequential probability ratio test for change detection and isolation", Abstract, Dept. of Mech. & Aerosp. Eng., California Univ., Los Angeles, CA, USA, Automatic Control, IEEE Transactions, Aug. 1999, 1 page.
(Continued)

*Primary Examiner* — Annette Dixon

(57) ABSTRACT

Systems and methods for triggering inspiration and/or cycling exhalation with a ventilator are described herein. In particular, systems and methods for synchronizing ventilator breath delivery with patient breath demand utilizing a digital sample counting trigger mode are described herein. The digital sample counting triggering mode characterizes digital samples taken from a measured or estimated parameter during the patient inhalation/exhalation period to synchronize breath delivery with patient breath demand.

20 Claims, 12 Drawing Sheets

(51) Int. Cl.
*A61B 5/08* (2006.01)
*A61B 5/113* (2006.01)

(52) U.S. Cl.
CPC .......... *A61B 5/4836* (2013.01); *A61B 5/7203* (2013.01); *A61B 5/7239* (2013.01); *A61B 5/7246* (2013.01); *A61B 5/7289* (2013.01); *A61M 16/0051* (2013.01); *A61B 5/113* (2013.01); *A61B 5/7278* (2013.01); *A61M 2016/0021* (2013.01); *A61M 2016/0027* (2013.01); *A61M 2016/0039* (2013.01); *A61M 2016/0042* (2013.01); *A61M 2205/3303* (2013.01); *A61M 2205/502* (2013.01); *A61M 2230/40* (2013.01)

(58) Field of Classification Search
USPC .......................... 128/204.18, 204.23, 204.26
See application file for complete search history.

(56) References Cited

U.S. PATENT DOCUMENTS

| | | |
|---|---|---|
| 3,586,021 A | 6/1971 | McGuinness |
| 3,633,576 A | 1/1972 | Gorsuch |
| 3,662,751 A | 5/1972 | Barkalow et al. |
| 3,664,370 A | 5/1972 | Warnow |
| 3,669,108 A | 6/1972 | Sundblom et al. |
| 3,677,267 A | 7/1972 | Richards |
| 3,695,263 A | 10/1972 | Kipling |
| 3,741,208 A | 6/1973 | Jonsson et al. |
| 3,753,436 A | 8/1973 | Bird et al. |
| 3,756,229 A | 9/1973 | Ollivier |
| 3,768,468 A | 10/1973 | Cox |
| 3,789,837 A | 2/1974 | Philips et al. |
| 3,834,382 A | 9/1974 | Lederman et al. |
| 3,889,669 A | 6/1975 | Weigl |
| 3,896,800 A | 7/1975 | Cibulka |
| 3,903,881 A | 9/1975 | Weigl |
| 3,905,362 A | 9/1975 | Eyrick et al. |
| 3,908,704 A | 9/1975 | Clement et al. |
| 3,910,261 A | 10/1975 | Ragsdale et al. |
| 3,961,627 A | 6/1976 | Ernst et al. |
| 3,976,052 A | 8/1976 | Junginger et al. |
| 3,981,301 A | 9/1976 | Warnow et al. |
| 4,003,377 A | 1/1977 | Dahl |
| 4,029,120 A | 6/1977 | Christianson |
| 4,044,763 A | 8/1977 | Bird |
| 4,050,458 A | 9/1977 | Friend |
| 4,060,078 A | 11/1977 | Bird |
| 4,095,592 A | 6/1978 | Delphia |
| 4,121,578 A | 10/1978 | Torzala |
| 4,155,357 A | 5/1979 | Dahl |
| 4,164,219 A | 8/1979 | Bird |
| 4,197,856 A | 4/1980 | Northrop |
| 4,211,221 A | 7/1980 | Schwanbom et al. |
| 4,275,722 A | 6/1981 | Sorensen |
| 4,281,651 A | 8/1981 | Cox |
| 4,323,064 A | 4/1982 | Hoenig et al. |
| 4,340,044 A | 7/1982 | Levy et al. |
| 4,351,344 A | 9/1982 | Stenzler |
| 4,401,115 A | 8/1983 | Monnier |
| 4,401,116 A | 8/1983 | Fry et al. |
| 4,421,113 A | 12/1983 | Gedeon et al. |
| 4,444,201 A | 4/1984 | Itoh |
| 4,459,982 A | 7/1984 | Fry |
| 4,459,983 A | 7/1984 | Beyreuther et al. |
| 4,539,984 A | 9/1985 | Kiszel et al. |
| 4,554,916 A | 11/1985 | Watt |
| 4,558,710 A | 12/1985 | Eichler |
| 4,566,450 A | 1/1986 | Brossman, Jr. |
| 4,598,706 A | 7/1986 | Darowski et al. |
| 4,612,928 A | 9/1986 | Tiep et al. |
| 4,640,277 A | 2/1987 | Meyer et al. |
| 4,648,407 A | 3/1987 | Sackner |
| 4,702,240 A | 10/1987 | Chaoui |
| 4,721,060 A | 1/1988 | Cannon et al. |
| 4,752,089 A | 6/1988 | Carter |
| 4,757,824 A | 7/1988 | Chaumet |
| 4,766,894 A | 8/1988 | Legrand et al. |
| 4,790,832 A | 12/1988 | Lopez |
| 4,796,618 A | 1/1989 | Garraffa |
| 4,870,961 A | 10/1989 | Barnard |
| 4,889,116 A | 12/1989 | Taube |
| 4,921,642 A | 5/1990 | LaTorraca |
| 4,954,799 A | 9/1990 | Kumar |
| 4,981,295 A | 1/1991 | Belman et al. |
| 4,982,735 A | 1/1991 | Yagata et al. |
| 5,007,420 A | 4/1991 | Bird |
| 5,016,626 A | 5/1991 | Jones |
| 5,057,822 A | 10/1991 | Hoffman |
| 5,072,737 A | 12/1991 | Goulding |
| 5,074,297 A | 12/1991 | Venegas |
| 5,080,093 A | 1/1992 | Raabe et al. |
| 5,086,767 A | 2/1992 | Legal |
| 5,099,837 A | 3/1992 | Russel, Sr. et al. |
| 5,117,818 A | 6/1992 | Palfy |
| 5,127,398 A | 7/1992 | Stone |
| 5,129,390 A | 7/1992 | Chopin et al. |
| 5,134,994 A | 8/1992 | Say |
| 5,148,802 A | 9/1992 | Sanders et al. |
| 5,150,291 A | 9/1992 | Cummings et al. |
| 5,154,167 A | 10/1992 | Hepburn |
| 5,161,525 A | 11/1992 | Kimm et al. |
| 5,165,397 A | 11/1992 | Arp |
| 5,165,398 A | 11/1992 | Bird |
| 5,174,284 A | 12/1992 | Jackson |
| 5,195,512 A | 3/1993 | Rosso |
| 5,211,170 A | 5/1993 | Press |
| 5,235,973 A | 8/1993 | Levinson |
| 5,237,987 A | 8/1993 | Anderson et al. |
| 5,239,995 A | 8/1993 | Estes et al. |
| 5,259,374 A | 11/1993 | Miller et al. |
| 5,271,389 A | 12/1993 | Isaza et al. |
| 5,273,032 A | 12/1993 | Borody |
| 5,279,549 A | 1/1994 | Ranford |
| 5,299,568 A | 4/1994 | Forare et al. |
| 5,301,921 A | 4/1994 | Kumar |
| 5,303,698 A | 4/1994 | Tobia et al. |
| 5,303,700 A | 4/1994 | Weismann et al. |
| 5,307,794 A | 5/1994 | Rauterkus et al. |
| 5,316,009 A | 5/1994 | Yamada |
| 5,318,017 A | 6/1994 | Ellison |
| 5,318,487 A | 6/1994 | Golen et al. |
| 5,319,540 A | 6/1994 | Isaza et al. |
| 5,320,093 A | 6/1994 | Raemer |
| 5,322,057 A | 6/1994 | Raabe et al. |
| 5,323,772 A | 6/1994 | Linden et al. |
| 5,325,861 A | 7/1994 | Goulding |
| 5,333,606 A | 8/1994 | Schneider et al. |
| 5,335,650 A | 8/1994 | Shaffer et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,373,842 A | 12/1994 | Olsson et al. |
| 5,383,448 A | 1/1995 | Tkatchouk et al. |
| 5,383,449 A | 1/1995 | Forare et al. |
| 5,385,142 A | 1/1995 | Brady et al. |
| 5,390,666 A | 2/1995 | Kimm et al. |
| 5,395,301 A | 3/1995 | Russek |
| 5,398,676 A | 3/1995 | Press et al. |
| 5,398,682 A | 3/1995 | Lynn |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,419,314 A | 5/1995 | Christopher |
| 5,429,123 A | 7/1995 | Shaffer et al. |
| 5,429,124 A | 7/1995 | Yoshida et al. |
| 5,433,193 A | 7/1995 | Sanders et al. |
| 5,435,305 A | 7/1995 | Rankin, Sr. |

(56) References Cited

U.S. PATENT DOCUMENTS

| | | | |
|---|---|---|---|
| 5,438,980 | A | 8/1995 | Phillips |
| 5,443,075 | A | 8/1995 | Holscher |
| 5,458,137 | A | 10/1995 | Axe et al. |
| 5,471,977 | A | 12/1995 | Olsson et al. |
| 5,474,062 | A | 12/1995 | DeVires et al. |
| 5,479,920 | A | 1/1996 | Piper et al. |
| 5,487,383 | A | 1/1996 | Levinson |
| 5,494,028 | A | 2/1996 | DeVries et al. |
| 5,513,631 | A | 5/1996 | McWilliams |
| 5,517,983 | A | 5/1996 | Deighan et al. |
| 5,520,071 | A | 5/1996 | Jones |
| 5,524,615 | A | 6/1996 | Power |
| 5,531,221 | A | 7/1996 | Power |
| 5,535,738 | A | 7/1996 | Estes et al. |
| 5,537,999 | A | 7/1996 | Dearman et al. |
| 5,540,220 | A | 7/1996 | Gropper et al. |
| 5,542,415 | A | 8/1996 | Brody |
| 5,542,416 | A | 8/1996 | Chalvignac |
| 5,544,674 | A | 8/1996 | Kelly |
| 5,549,106 | A | 8/1996 | Gruenke et al. |
| 5,549,655 | A | 8/1996 | Erickson |
| 5,551,418 | A | 9/1996 | Estes et al. |
| 5,551,419 | A * | 9/1996 | Froehlich .......... A61M 16/0069 128/204.23 |
| 5,558,086 | A | 9/1996 | Smith et al. |
| 5,562,918 | A | 10/1996 | Stimpson |
| 5,564,416 | A | 10/1996 | Jones |
| 5,582,163 | A | 12/1996 | Bonassa |
| 5,590,651 | A | 1/1997 | Shaffer et al. |
| 5,596,983 | A | 1/1997 | Zander et al. |
| 5,596,984 | A | 1/1997 | O'Mahony et al. |
| 5,603,315 | A | 2/1997 | Sasso, Jr. |
| 5,603,316 | A | 2/1997 | Coufal et al. |
| 5,606,968 | A | 3/1997 | Mang |
| 5,630,411 | A | 5/1997 | Holscher |
| 5,632,269 | A | 5/1997 | Zdrojkowski |
| 5,632,270 | A | 5/1997 | O'Mahony et al. |
| 5,642,726 | A | 7/1997 | Owens et al. |
| 5,645,048 | A | 7/1997 | Brodsky et al. |
| 5,645,053 | A | 7/1997 | Remmers et al. |
| 5,647,345 | A | 7/1997 | Saul |
| 5,647,351 | A | 7/1997 | Weismann et al. |
| 5,651,361 | A | 7/1997 | Dearman et al. |
| 5,655,519 | A | 8/1997 | Alfery |
| 5,660,171 | A | 8/1997 | Kimm et al. |
| 5,664,560 | A | 9/1997 | Merrick et al. |
| 5,664,562 | A | 9/1997 | Bourdon |
| 5,669,379 | A | 9/1997 | Somerson et al. |
| 5,671,767 | A | 9/1997 | Kelly |
| 5,672,041 | A | 9/1997 | Ringdahl et al. |
| 5,673,689 | A | 10/1997 | Power |
| 5,687,713 | A | 11/1997 | Bahr et al. |
| 5,692,497 | A | 12/1997 | Schnitzer et al. |
| 5,706,799 | A | 1/1998 | Imai et al. |
| 5,715,812 | A | 2/1998 | Deighan et al. |
| 5,720,277 | A | 2/1998 | Olsson et al. |
| 5,724,962 | A | 3/1998 | Vidgren et al. |
| 5,727,562 | A | 3/1998 | Beck |
| 5,735,267 | A | 4/1998 | Tobia |
| 5,738,090 | A | 4/1998 | Lachmann et al. |
| 5,740,795 | A | 4/1998 | Brydon |
| 5,740,796 | A | 4/1998 | Skog |
| 5,740,797 | A | 4/1998 | Dickson |
| 5,752,509 | A | 5/1998 | Lachmann et al. |
| 5,762,480 | A | 6/1998 | Adahan |
| 5,765,558 | A | 6/1998 | Psaros et al. |
| 5,771,884 | A | 6/1998 | Yarnall et al. |
| 5,791,339 | A | 8/1998 | Winter |
| 5,794,615 | A | 8/1998 | Estes |
| 5,794,986 | A | 8/1998 | Gansel et al. |
| 5,803,065 | A | 9/1998 | Zdrojkowski et al. |
| 5,803,066 | A | 9/1998 | Rapoport et al. |
| 5,806,512 | A | 9/1998 | Abramov et al. |
| 5,807,245 | A | 9/1998 | Aldestam et al. |
| 5,810,000 | A | 9/1998 | Stevens |
| 5,813,399 | A | 9/1998 | Isaza et al. |
| 5,813,401 | A | 9/1998 | Radcliff et al. |
| 5,814,086 | A | 9/1998 | Hirschberg et al. |
| 5,826,575 | A | 10/1998 | Lall |
| 5,829,441 | A | 11/1998 | Kidd et al. |
| 5,864,938 | A | 2/1999 | Gansel et al. |
| 5,865,168 | A | 2/1999 | Isaza |
| 5,865,173 | A | 2/1999 | Froehlich |
| 5,868,133 | A | 2/1999 | DeVries et al. |
| 5,876,352 | A | 3/1999 | Weismann |
| 5,878,744 | A | 3/1999 | Pfeiffer |
| 5,881,717 | A | 3/1999 | Isaza |
| 5,881,723 | A | 3/1999 | Wallace et al. |
| 5,881,725 | A | 3/1999 | Hoffman et al. |
| 5,884,623 | A | 3/1999 | Winter |
| 5,906,203 | A | 5/1999 | Klockseth et al. |
| 5,909,731 | A | 6/1999 | O'Mahony et al. |
| 5,911,218 | A | 6/1999 | DiMarco |
| 5,915,379 | A | 6/1999 | Wallace et al. |
| 5,915,380 | A | 6/1999 | Wallace et al. |
| 5,915,381 | A | 6/1999 | Nord |
| 5,915,382 | A | 6/1999 | Power |
| 5,918,597 | A | 7/1999 | Jones et al. |
| 5,921,238 | A | 7/1999 | Bourdon |
| 5,927,274 | A | 7/1999 | Servidio et al. |
| 5,931,160 | A | 8/1999 | Gilmore et al. |
| 5,931,162 | A | 8/1999 | Christian |
| 5,934,274 | A | 8/1999 | Merrick et al. |
| 5,937,853 | A | 8/1999 | Strom |
| 5,944,680 | A | 8/1999 | Christopherson |
| 5,970,975 | A | 10/1999 | Estes et al. |
| 5,996,580 | A | 12/1999 | Swann |
| 6,015,388 | A | 1/2000 | Sackner et al. |
| 6,019,100 | A | 2/2000 | Alving et al. |
| 6,024,089 | A | 2/2000 | Wallace et al. |
| 6,029,664 | A | 2/2000 | Zdrojkowski et al. |
| 6,029,665 | A | 2/2000 | Berton-Jones |
| 6,041,780 | A | 3/2000 | Richard et al. |
| 6,044,841 | A | 4/2000 | Verdun et al. |
| 6,047,860 | A | 4/2000 | Sanders |
| 6,066,101 | A | 5/2000 | Johnson et al. |
| 6,068,602 | A | 5/2000 | Tham et al. |
| 6,076,519 | A | 6/2000 | Johnson |
| 6,076,523 | A | 6/2000 | Jones et al. |
| 6,095,140 | A | 8/2000 | Poon et al. |
| 6,109,260 | A | 8/2000 | Bathe |
| 6,112,744 | A | 9/2000 | Hognelid |
| 6,116,240 | A | 9/2000 | Merrick et al. |
| 6,116,464 | A | 9/2000 | Sanders |
| 6,123,073 | A | 9/2000 | Schlawin et al. |
| 6,131,571 | A | 10/2000 | Lampotang et al. |
| 6,131,572 | A | 10/2000 | Heinonen |
| 6,135,105 | A | 10/2000 | Lampotang et al. |
| 6,135,106 | A | 10/2000 | Dirks et al. |
| 6,138,675 | A | 10/2000 | Berthon-Jones |
| 6,142,150 | A | 11/2000 | O'Mahoney et al. |
| 6,148,814 | A | 11/2000 | Clemmer et al. |
| 6,152,129 | A | 11/2000 | Berthon Jones |
| 6,152,133 | A | 11/2000 | Psaros et al. |
| 6,152,135 | A | 11/2000 | DeVries et al. |
| 6,155,257 | A | 12/2000 | Lurie et al. |
| 6,158,432 | A | 12/2000 | Biondi et al. |
| 6,158,433 | A | 12/2000 | Ong et al. |
| 6,161,539 | A | 12/2000 | Winter |
| 6,192,885 | B1 | 2/2001 | Jalde |
| 6,196,222 | B1 | 3/2001 | Heinonen et al. |
| 6,213,119 | B1 | 4/2001 | Brydon et al. |
| 6,220,244 | B1 | 4/2001 | McLaughlin |
| 6,220,245 | B1 | 4/2001 | Takabayashi et al. |
| 6,230,708 | B1 | 5/2001 | Radko |
| 6,257,234 | B1 | 7/2001 | Sun |
| 6,260,549 | B1 | 7/2001 | Sosiak |
| 6,269,812 | B1 | 8/2001 | Wallace et al. |
| 6,273,444 | B1 | 8/2001 | Power |
| 6,279,569 | B1 | 8/2001 | Berthon Jones |
| 6,279,574 | B1 | 8/2001 | Richardson et al. |
| 6,283,119 | B1 | 9/2001 | Bourdon |
| 6,305,373 | B1 | 10/2001 | Wallace et al. |
| 6,305,374 | B1 | 10/2001 | Zdrojkowski et al. |

(56) References Cited

U.S. PATENT DOCUMENTS

| | | |
|---|---|---|
| 6,308,703 B1 | 10/2001 | Alving et al. |
| 6,308,706 B1 | 10/2001 | Lammers et al. |
| 6,318,365 B1 | 11/2001 | Vogele et al. |
| 6,321,748 B1 | 11/2001 | O'Mahoney |
| 6,325,785 B1 | 12/2001 | Babkes et al. |
| 6,343,603 B1 | 2/2002 | Tuck et al. |
| 6,345,619 B1 | 2/2002 | Finn |
| 6,357,438 B1 | 3/2002 | Hansen |
| 6,360,740 B1 | 3/2002 | Ward et al. |
| 6,360,745 B1 | 3/2002 | Wallace et al. |
| 6,369,838 B1 | 4/2002 | Wallace et al. |
| 6,390,091 B1 | 5/2002 | Banner et al. |
| 6,390,988 B1 | 5/2002 | Robinson |
| 6,408,847 B1 | 6/2002 | Nuckols et al. |
| 6,412,482 B1 | 7/2002 | Rowe |
| 6,412,483 B1 | 7/2002 | Jones et al. |
| 6,425,392 B1 | 7/2002 | Sosiak |
| 6,439,229 B1 | 8/2002 | Du et al. |
| 6,450,163 B1 | 9/2002 | Blacker et al. |
| 6,450,968 B1 | 9/2002 | Wallen et al. |
| 6,461,315 B1 | 10/2002 | Gattinoni |
| 6,463,930 B2 | 10/2002 | Biondi et al. |
| 6,467,477 B1 | 10/2002 | Frank et al. |
| 6,467,478 B1 | 10/2002 | Merrick et al. |
| 6,467,479 B1 | 10/2002 | Albert et al. |
| 6,484,719 B1 | 11/2002 | Berthon Jones |
| 6,494,201 B1 | 12/2002 | Welik |
| 6,512,938 B2 | 1/2003 | Claure et al. |
| 6,516,800 B1 | 2/2003 | Bowden |
| 6,517,497 B2 | 2/2003 | Rymut et al. |
| 6,523,538 B1 | 2/2003 | Wikfeldt |
| 6,526,970 B2 | 3/2003 | DeVries et al. |
| 6,532,956 B2 | 3/2003 | Hill |
| 6,532,957 B2 | 3/2003 | Berthon Jones |
| 6,532,959 B1 | 3/2003 | Berthon Jones |
| 6,537,228 B1 | 3/2003 | Lambert |
| 6,539,938 B2 | 4/2003 | Weinstein et al. |
| 6,539,940 B2 | 4/2003 | Zdrojkowski et al. |
| 6,546,930 B1 | 4/2003 | Emerson et al. |
| 6,547,743 B2 | 4/2003 | Brydon |
| 6,553,991 B1 | 4/2003 | Isaza |
| 6,553,992 B1 | 4/2003 | Berthon Jones et al. |
| 6,557,553 B1 | 5/2003 | Borrello |
| 6,564,798 B1 | 5/2003 | Jalde |
| 6,571,795 B2 | 6/2003 | Bourdon |
| 6,571,796 B2 | 6/2003 | Banner et al. |
| 6,575,163 B1 | 6/2003 | Berthon Jones |
| 6,575,164 B1 | 6/2003 | Jaffe et al. |
| 6,578,575 B1 | 6/2003 | Jonson |
| 6,581,599 B1 | 6/2003 | Stenzler |
| 6,588,423 B1 | 7/2003 | Sinderby |
| 6,595,212 B1 | 7/2003 | Arnott |
| 6,595,213 B2 | 7/2003 | Bennarsten |
| 6,601,583 B2 | 8/2003 | Pessala et al. |
| 6,609,517 B1 | 8/2003 | Estes et al. |
| 6,609,518 B2 | 8/2003 | Lamb |
| 6,622,725 B1 | 9/2003 | Fisher et al. |
| 6,622,726 B1 | 9/2003 | Du |
| 6,626,175 B2 | 9/2003 | Jafari et al. |
| 6,631,716 B1 | 10/2003 | Robinson et al. |
| 6,631,717 B1 | 10/2003 | Rich et al. |
| 6,644,310 B1 | 11/2003 | Delache et al. |
| 6,651,652 B1 | 11/2003 | Ward |
| 6,659,101 B2 | 12/2003 | Berthon Jones |
| 6,659,961 B2 | 12/2003 | Robinson |
| 6,668,824 B1 | 12/2003 | Isaza et al. |
| 6,668,829 B2 | 12/2003 | Biondi et al. |
| 6,671,529 B2 | 12/2003 | Claure et al. |
| 6,675,801 B2 | 1/2004 | Wallace et al. |
| 6,679,258 B1 | 1/2004 | Strom |
| 6,681,643 B2 | 1/2004 | Heinonen |
| 6,688,307 B2 | 2/2004 | Berthon Jones |
| 6,689,091 B2 | 2/2004 | Bui et al. |
| 6,694,978 B1 | 2/2004 | Bennarsten |
| 6,718,974 B1 | 4/2004 | Moberg |
| 6,722,360 B2 | 4/2004 | Doshi |
| 6,725,447 B1 | 4/2004 | Gilman et al. |
| 6,726,598 B1 | 4/2004 | Jarvis et al. |
| 6,739,337 B2 | 5/2004 | Isaza |
| 6,745,771 B2 | 6/2004 | Castor et al. |
| 6,745,773 B1 | 6/2004 | Gobel |
| 6,752,766 B2 | 6/2004 | Kowallik et al. |
| 6,752,772 B2 | 6/2004 | Kahn |
| 6,755,193 B2 | 6/2004 | Berthon Jones et al. |
| 6,758,216 B1 | 7/2004 | Berthon Jones et al. |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,786,217 B2 | 9/2004 | Stenzler |
| 6,796,305 B1 | 9/2004 | Banner et al. |
| 6,805,118 B2 | 10/2004 | Brooker et al. |
| 6,810,876 B2 | 11/2004 | Berthon Jones |
| 6,814,074 B1 | 11/2004 | Nadjafizadeh et al. |
| 6,814,075 B2 | 11/2004 | Boussignac |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,834,647 B2 | 12/2004 | Blair et al. |
| 6,837,241 B2 | 1/2005 | Samzelius |
| 6,837,242 B2 | 1/2005 | Younes |
| 6,840,240 B1 | 1/2005 | Berthon Jones et al. |
| 6,851,427 B1 | 2/2005 | Nashed |
| 6,860,264 B2 | 3/2005 | Christopher |
| 6,860,265 B1 | 3/2005 | Emerson |
| 6,860,858 B2 | 3/2005 | Green et al. |
| 6,863,068 B2 | 3/2005 | Jamison et al. |
| 6,863,656 B2 | 3/2005 | Lurie |
| 6,866,040 B1 | 3/2005 | Bourdon |
| 6,877,511 B2 | 4/2005 | DeVries et al. |
| 6,910,480 B1 | 6/2005 | Berthon Jones |
| 6,920,875 B1 | 7/2005 | Hill et al. |
| 6,920,878 B2 | 7/2005 | Sinderby et al. |
| 6,938,619 B1 | 9/2005 | Hickle |
| 6,948,497 B2 | 9/2005 | Zdrojkowski et al. |
| 6,960,854 B2 | 11/2005 | Nadjafizadeh et al. |
| 6,976,487 B1 | 12/2005 | Melker et al. |
| 6,988,498 B2 | 1/2006 | Berthon-Jones et al. |
| 6,990,980 B2 | 1/2006 | Richey, II |
| 6,997,881 B2 | 2/2006 | Green et al. |
| 7,000,612 B2 | 2/2006 | Jafari et al. |
| 7,001,339 B2 | 2/2006 | Lin |
| 7,001,340 B2 | 2/2006 | Lin |
| 7,008,380 B1 | 3/2006 | Rees et al. |
| 7,011,091 B2 | 3/2006 | Hill et al. |
| 7,011,092 B2 | 3/2006 | McCombs et al. |
| 7,013,892 B2 | 3/2006 | Estes et al. |
| 7,017,574 B2 | 3/2006 | Biondi et al. |
| 7,036,504 B2 | 5/2006 | Wallace et al. |
| 7,040,321 B2 | 5/2006 | Gobel et al. |
| 7,051,736 B2 | 5/2006 | Banner et al. |
| 7,055,522 B2 | 6/2006 | Berthon Jones |
| 7,066,173 B2 | 6/2006 | Banner et al. |
| 7,066,175 B2 | 6/2006 | Hamilton et al. |
| 7,066,176 B2 | 6/2006 | Jaffe et al. |
| 7,070,570 B2 | 7/2006 | Sanderson et al. |
| 7,077,131 B2 | 7/2006 | Hansen |
| 7,077,132 B2 | 7/2006 | Berthon-Jones |
| 7,080,646 B2 | 7/2006 | Wiesmann et al. |
| RE39,225 E | 8/2006 | Isaza et al. |
| 7,087,027 B2 | 8/2006 | Page |
| 7,089,932 B2 | 8/2006 | Dodds |
| 7,100,607 B2 | 9/2006 | Zdrojkowski et al. |
| 7,100,609 B2 | 9/2006 | Berthon Jones et al. |
| 7,104,962 B2 | 9/2006 | Lomask et al. |
| 7,117,438 B2 | 10/2006 | Wallace et al. |
| 7,121,277 B2 | 10/2006 | Ström |
| 7,128,069 B2 | 10/2006 | Farrugia et al. |
| 7,137,389 B2 | 11/2006 | Berthon Jones |
| 7,152,598 B2 | 12/2006 | Morris et al. |
| 7,152,604 B2 | 12/2006 | Hickle et al. |
| 7,156,095 B2 | 1/2007 | Melker et al. |
| 7,162,296 B2 | 1/2007 | Leonhardt et al. |
| 7,191,780 B2 | 3/2007 | Faram |
| 7,210,478 B2 | 5/2007 | Banner et al. |

(56) References Cited

U.S. PATENT DOCUMENTS

| | | |
|---|---|---|
| 7,211,049 B2 | 5/2007 | Bradley et al. |
| 7,226,427 B2 | 6/2007 | Steen |
| 7,255,103 B2 | 8/2007 | Bassin |
| 7,267,652 B2 | 9/2007 | Coyle et al. |
| 7,270,126 B2 | 9/2007 | Wallace et al. |
| 7,275,540 B2 | 10/2007 | Bolam et al. |
| 7,276,031 B2 | 10/2007 | Norman et al. |
| 7,311,668 B2 | 12/2007 | Lurie |
| 7,334,578 B2 | 2/2008 | Biondi et al. |
| 7,334,581 B2 | 2/2008 | Doshi |
| 7,347,205 B2 | 3/2008 | Levi |
| 7,363,925 B2 | 4/2008 | Pagan |
| 7,367,337 B2 | 5/2008 | Berthon Jones et al. |
| 7,369,757 B2 | 5/2008 | Farbarik |
| 7,370,650 B2 | 5/2008 | Nadjafizadeh et al. |
| 7,390,304 B2 | 6/2008 | Chen et al. |
| 7,392,806 B2 | 7/2008 | Yuen et al. |
| 7,422,015 B2 | 9/2008 | Delisle et al. |
| 7,425,201 B2 | 9/2008 | Euliano et al. |
| 7,428,902 B2 | 9/2008 | Du et al. |
| 7,445,006 B2 | 11/2008 | Dhuper et al. |
| 7,460,959 B2 | 12/2008 | Jafari |
| 7,464,711 B2 | 12/2008 | Flodin |
| 7,467,012 B1 | 12/2008 | Park et al. |
| 7,472,702 B2 | 1/2009 | Beck et al. |
| 7,484,508 B2 | 2/2009 | Younes |
| 7,487,773 B2 | 2/2009 | Li |
| 7,487,774 B2 | 2/2009 | Acker |
| 7,487,775 B2 | 2/2009 | Mashak |
| 7,509,957 B2 | 3/2009 | Duquette et al. |
| 7,523,752 B2 | 4/2009 | Montgomery et al. |
| 7,530,353 B2 | 5/2009 | Choncholas et al. |
| 7,547,285 B2 | 6/2009 | Kline |
| 7,549,421 B2 | 6/2009 | Levi et al. |
| 7,552,731 B2 | 6/2009 | Jorczak et al. |
| 7,556,038 B2 | 7/2009 | Kirby et al. |
| 7,559,326 B2 | 7/2009 | Smith et al. |
| 7,572,225 B2 | 8/2009 | Stahmann et al. |
| 7,574,246 B2 | 8/2009 | Krebs et al. |
| 7,584,752 B2 | 9/2009 | Garber et al. |
| 7,588,033 B2 | 9/2009 | Wondka |
| 7,588,543 B2 | 9/2009 | Euliano et al. |
| 7,594,508 B2 | 9/2009 | Doyle |
| 7,610,914 B2 | 11/2009 | Bolam et al. |
| 7,617,821 B2 | 11/2009 | Hughes |
| 7,617,825 B2 | 11/2009 | Pedemonte |
| 7,621,270 B2 | 11/2009 | Morris et al. |
| 7,624,736 B2 | 12/2009 | Borody |
| 7,634,998 B1 | 12/2009 | Fenley |
| 7,644,713 B2 | 1/2010 | Berthon Jones |
| 7,654,802 B2 | 2/2010 | Crawford, Jr. et al. |
| 7,669,594 B2 | 3/2010 | Downie |
| 7,669,598 B2 | 3/2010 | Rick et al. |
| 7,678,061 B2 | 3/2010 | Lee et al. |
| 7,682,312 B2 | 3/2010 | Lurie |
| 7,694,677 B2 | 4/2010 | Tang |
| 7,694,682 B2 | 4/2010 | Petersen et al. |
| 7,717,110 B2 | 5/2010 | Kane et al. |
| 7,717,113 B2 | 5/2010 | Andrieux |
| 7,721,736 B2 | 5/2010 | Urias et al. |
| 7,722,546 B2 | 5/2010 | Madaus et al. |
| D618,356 S | 6/2010 | Ross |
| 7,727,160 B2 | 6/2010 | Green et al. |
| 7,730,886 B2 | 6/2010 | Berthon-Jones |
| 7,731,663 B2 | 6/2010 | Averina et al. |
| 7,735,486 B2 | 6/2010 | Payne |
| 7,735,492 B2 | 6/2010 | Doshi et al. |
| 7,775,207 B2 | 8/2010 | Jaffe et al. |
| 7,784,461 B2 | 8/2010 | Figueiredo et al. |
| 7,793,656 B2 | 9/2010 | Johnson |
| 7,798,145 B2 | 9/2010 | Weismann et al. |
| 7,802,571 B2 | 9/2010 | Tehrani |
| 7,809,442 B2 | 10/2010 | Bolea et al. |
| 7,810,496 B2 | 10/2010 | Estes et al. |
| 7,810,497 B2 | 10/2010 | Pittman et al. |
| 7,810,498 B1 | 10/2010 | Patterson |
| 7,814,906 B2 | 10/2010 | Moretti |
| 7,819,815 B2 | 10/2010 | Younes |
| 7,823,588 B2 | 11/2010 | Hansen |
| 7,841,341 B2 | 11/2010 | Dhuper et al. |
| 7,850,619 B2 | 12/2010 | Gavish et al. |
| 7,855,716 B2 | 12/2010 | McCreary et al. |
| 7,865,244 B2 | 1/2011 | Giftakis et al. |
| 7,866,318 B2 | 1/2011 | Bassin |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,938,114 B2 | 5/2011 | Matthews et al. |
| 7,963,283 B2 | 6/2011 | Sinderby |
| 7,970,475 B2 | 6/2011 | Tehrani et al. |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 7,997,271 B2 | 8/2011 | Hickle et al. |
| 8,001,967 B2 | 8/2011 | Wallace et al. |
| D645,158 S | 9/2011 | Sanchez et al. |
| 8,021,308 B2 | 9/2011 | Carlson et al. |
| 8,021,309 B2 | 9/2011 | Zilberg |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,231,536 B2 | 7/2012 | Cho et al. |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| 8,597,185 B2 | 12/2013 | Pipke |
| 8,603,006 B2 | 12/2013 | Mulqueeny et al. |
| D701,601 S | 3/2014 | Winter |
| 8,792,949 B2 | 7/2014 | Baker, Jr. |
| 2001/0004893 A1 | 6/2001 | Biondi et al. |
| 2001/0007255 A1 | 7/2001 | Stumpf |
| 2002/0017301 A1 | 2/2002 | Lundin |
| 2002/0023640 A1 | 2/2002 | Nightengale |
| 2002/0026941 A1 | 3/2002 | Biondi et al. |
| 2002/0042564 A1 | 4/2002 | Cooper et al. |
| 2002/0042565 A1 | 4/2002 | Cooper et al. |
| 2002/0046753 A1 | 4/2002 | Lamb |
| 2002/0072685 A1 | 6/2002 | Rymut et al. |
| 2002/0073993 A1 | 6/2002 | Weinstein et al. |
| 2002/0174866 A1 | 11/2002 | Orr et al. |
| 2002/0185126 A1 | 12/2002 | Krebs |
| 2002/0195105 A1 | 12/2002 | Blue et al. |
| 2003/0010339 A1 | 1/2003 | Banner et al. |
| 2003/0034031 A1 | 2/2003 | Lev et al. |
| 2003/0037786 A1 | 2/2003 | Biondi et al. |
| 2003/0125662 A1 | 7/2003 | Bui |
| 2003/0131848 A1 | 7/2003 | Stenzler |
| 2003/0136402 A1 | 7/2003 | Jiang et al. |
| 2003/0140925 A1 | 7/2003 | Sapienza et al. |
| 2003/0145853 A1 | 8/2003 | Muellner |
| 2003/0154979 A1 | 8/2003 | Berthon Jones |
| 2003/0159695 A1 | 8/2003 | Younes |
| 2003/0172929 A1 | 9/2003 | Muellner |
| 2003/0178024 A1 | 9/2003 | Allan et al. |
| 2003/0192544 A1 | 10/2003 | Berthon Jones et al. |

(56) References Cited

U.S. PATENT DOCUMENTS

| | | |
|---|---|---|
| 2003/0216660 A1 | 11/2003 | Ben-Oren et al. |
| 2003/0225339 A1 | 12/2003 | Orr et al. |
| 2004/0016431 A1 | 1/2004 | Preveyraud |
| 2004/0103896 A1 | 6/2004 | Jafari et al. |
| 2004/0133123 A1 | 7/2004 | Leonhardt et al. |
| 2004/0149282 A1 | 8/2004 | Hickle |
| 2004/0159323 A1 | 8/2004 | Schmidt et al. |
| 2004/0187864 A1 | 9/2004 | Adams |
| 2004/0194779 A1 | 10/2004 | Doshi |
| 2004/0194780 A1 | 10/2004 | Doshi |
| 2004/0200477 A1 | 10/2004 | Bleys et al. |
| 2004/0206355 A1 | 10/2004 | Berthon Jones et al. |
| 2004/0221847 A1 | 11/2004 | Berthon Jones et al. |
| 2004/0231670 A1 | 11/2004 | Bassin |
| 2004/0244804 A1 | 12/2004 | Olsen et al. |
| 2005/0022809 A1 | 2/2005 | Wondka |
| 2005/0027252 A1 | 2/2005 | Boukas |
| 2005/0039748 A1 | 2/2005 | Andrieux |
| 2005/0061318 A1 | 3/2005 | Faram |
| 2005/0076907 A1 | 4/2005 | Stenzler |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0098179 A1 | 5/2005 | Burton et al. |
| 2005/0103331 A1 | 5/2005 | Wedemeyer |
| 2005/0109339 A1 | 5/2005 | Stahmann et al. |
| 2005/0109340 A1 | 5/2005 | Tehrani |
| 2005/0126565 A1 | 6/2005 | Huang |
| 2005/0133028 A1 | 6/2005 | Pagan |
| 2005/0139212 A1 | 6/2005 | Bourdon |
| 2005/0199237 A1 | 9/2005 | Lurie |
| 2005/0217671 A1 | 10/2005 | Fisher et al. |
| 2005/0241639 A1 | 11/2005 | Zilberg |
| 2005/0263152 A1 | 12/2005 | Fong |
| 2005/0279358 A1 | 12/2005 | Richey, II |
| 2005/0284469 A1 | 12/2005 | Tobia et al. |
| 2006/0011195 A1 | 1/2006 | Zarychta |
| 2006/0021618 A1 | 2/2006 | Berthon-Jones et al. |
| 2006/0021620 A1 | 2/2006 | Calluaud et al. |
| 2006/0032497 A1 | 2/2006 | Doshi |
| 2006/0094972 A1 | 5/2006 | Drew |
| 2006/0102180 A1 | 5/2006 | Berthon Jones |
| 2006/0122662 A1 | 6/2006 | Tehrani et al. |
| 2006/0142815 A1 | 6/2006 | Tehrani et al. |
| 2006/0162727 A1 | 7/2006 | Biondi et al. |
| 2006/0178245 A1 | 8/2006 | Schiller et al. |
| 2006/0196507 A1 | 9/2006 | Bradley |
| 2006/0196508 A1 | 9/2006 | Chalvignac |
| 2006/0201507 A1 | 9/2006 | Breen |
| 2006/0241708 A1 | 10/2006 | Boute |
| 2006/0249148 A1 | 11/2006 | Younes |
| 2006/0249155 A1 | 11/2006 | Gambone |
| 2006/0272642 A1 | 12/2006 | Chalvignac |
| 2006/0276718 A1 | 12/2006 | Madaus et al. |
| 2006/0278221 A1 | 12/2006 | Schermeier et al. |
| 2006/0278224 A1 | 12/2006 | Shaffer et al. |
| 2006/0283450 A1 | 12/2006 | Shissler et al. |
| 2006/0283451 A1 | 12/2006 | Albertelli |
| 2007/0000494 A1 | 1/2007 | Banner et al. |
| 2007/0017515 A1 | 1/2007 | Wallace et al. |
| 2007/0017518 A1 | 1/2007 | Farrugia et al. |
| 2007/0028921 A1 | 2/2007 | Banner et al. |
| 2007/0044796 A1 | 3/2007 | Zdrojkowski et al. |
| 2007/0062529 A1 | 3/2007 | Choncholas et al. |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0077200 A1 | 4/2007 | Baker |
| 2007/0113843 A1 | 5/2007 | Hughes |
| 2007/0123792 A1 | 5/2007 | Kline |
| 2007/0129646 A1 | 6/2007 | Heinonen et al. |
| 2007/0144523 A1 | 6/2007 | Bolam et al. |
| 2007/0151563 A1 | 7/2007 | Ozaki et al. |
| 2007/0157931 A1 | 7/2007 | Parker et al. |
| 2007/0163590 A1 | 7/2007 | Bassin |
| 2007/0181122 A1 | 8/2007 | Mulier |
| 2007/0186928 A1 | 8/2007 | Be'Eri |
| 2007/0191787 A1 | 8/2007 | Lim et al. |
| 2007/0208267 A1 | 9/2007 | Schmid et al. |
| 2007/0221222 A1 | 9/2007 | Lurie |
| 2007/0225623 A1 | 9/2007 | Freeman |
| 2007/0227537 A1 | 10/2007 | Bemister et al. |
| 2007/0227538 A1 | 10/2007 | Scholler et al. |
| 2007/0227539 A1 | 10/2007 | Schwaibold et al. |
| 2007/0267015 A1 | 11/2007 | Thoemmes et al. |
| 2007/0272241 A1 | 11/2007 | Sanborn et al. |
| 2007/0272243 A1 | 11/2007 | Sherman et al. |
| 2007/0277825 A1 | 12/2007 | Bordewick et al. |
| 2007/0284361 A1 | 12/2007 | Nadjafizadeh et al. |
| 2008/0000471 A1 | 1/2008 | Bolam et al. |
| 2008/0000475 A1 | 1/2008 | Hill |
| 2008/0000478 A1 | 1/2008 | Matthiessen et al. |
| 2008/0011294 A1 | 1/2008 | Heesch et al. |
| 2008/0017198 A1 | 1/2008 | Ivri |
| 2008/0029096 A1 | 2/2008 | Kollmeyer et al. |
| 2008/0033304 A1 | 2/2008 | Dalal et al. |
| 2008/0035146 A1 | 2/2008 | Crabb |
| 2008/0041382 A1 | 2/2008 | Matthews et al. |
| 2008/0041383 A1 | 2/2008 | Matthews et al. |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110462 A1 | 5/2008 | Chekal et al. |
| 2008/0115786 A1 | 5/2008 | Sinderby et al. |
| 2008/0125828 A1 | 5/2008 | Ignagni et al. |
| 2008/0135044 A1 | 6/2008 | Freitag et al. |
| 2008/0139956 A1 | 6/2008 | Diong |
| 2008/0142019 A1 | 6/2008 | Lewis et al. |
| 2008/0156330 A1 | 7/2008 | Smith et al. |
| 2008/0163872 A1 | 7/2008 | Negele et al. |
| 2008/0168990 A1 | 7/2008 | Cooke et al. |
| 2008/0178880 A1 | 7/2008 | Christopher et al. |
| 2008/0178882 A1 | 7/2008 | Christopher et al. |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0202525 A1 | 8/2008 | Mitton et al. |
| 2008/0208281 A1 | 8/2008 | Tehrani et al. |
| 2008/0216833 A1 | 9/2008 | Pujol et al. |
| 2008/0251078 A1 | 10/2008 | Buckley et al. |
| 2008/0257337 A1 | 10/2008 | Denyer et al. |
| 2008/0275513 A1 | 11/2008 | Lattner et al. |
| 2008/0276940 A1 | 11/2008 | Fuhrman et al. |
| 2008/0281219 A1 | 11/2008 | Glickman et al. |
| 2008/0283060 A1 | 11/2008 | Bassin |
| 2008/0283061 A1 | 11/2008 | Tiedje |
| 2008/0294060 A1 | 11/2008 | Haro et al. |
| 2008/0295837 A1 | 12/2008 | McCormick et al. |
| 2008/0295839 A1 | 12/2008 | Habashi |
| 2008/0295840 A1 | 12/2008 | Glaw |
| 2009/0007914 A1 | 1/2009 | Bateman |
| 2009/0013999 A1 | 1/2009 | Bassin |
| 2009/0038617 A1 | 2/2009 | Berthon-Jones et al. |
| 2009/0056709 A1 | 3/2009 | Worsoff |
| 2009/0095297 A1 | 4/2009 | Hallett |
| 2009/0114223 A1 | 5/2009 | Bonassa |
| 2009/0120439 A1 | 5/2009 | Goebel |
| 2009/0137919 A1 | 5/2009 | Bar-Lavie et al. |
| 2009/0139522 A1 | 6/2009 | Thomson et al. |
| 2009/0165795 A1 | 7/2009 | Nadjafizadeh et al. |
| 2009/0171176 A1 | 7/2009 | Andersohn |
| 2009/0205660 A1 | 8/2009 | Thomson et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |

(56) References Cited

U.S. PATENT DOCUMENTS

| | | |
|---|---|---|
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0266360 A1 | 10/2009 | Acker et al. |
| 2009/0277448 A1 | 11/2009 | Ahlmén et al. |
| 2009/0301486 A1 | 12/2009 | Masic |
| 2009/0301487 A1 | 12/2009 | Masic |
| 2009/0301488 A1 | 12/2009 | Sun |
| 2009/0301490 A1 | 12/2009 | Masic |
| 2009/0301491 A1 | 12/2009 | Masic et al. |
| 2009/0308393 A1 | 12/2009 | Luceros |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0076322 A1 | 3/2010 | Shrivastav et al. |
| 2010/0076323 A1 | 3/2010 | Shrivastav et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0089396 A1 | 4/2010 | Richard et al. |
| 2010/0108066 A1 | 5/2010 | Martin et al. |
| 2010/0116270 A1 | 5/2010 | Edwards et al. |
| 2010/0125227 A1 | 5/2010 | Bird |
| 2010/0139660 A1 | 6/2010 | Adahan |
| 2010/0145211 A1 | 6/2010 | Yamamori |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0229863 A1 | 9/2010 | Enk |
| 2010/0236551 A1 | 9/2010 | Enk |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252046 A1 | 10/2010 | Dahlström et al. |
| 2010/0258124 A1 | 10/2010 | Madaus et al. |
| 2010/0263669 A1 | 10/2010 | Bowsher |
| 2010/0275921 A1* | 11/2010 | Schindhelm ............ A61B 5/08 128/204.23 |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0011403 A1 | 1/2011 | Hannah et al. |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0030686 A1 | 2/2011 | Wilkinson et al. |
| 2011/0041849 A1 | 2/2011 | Chen et al. |
| 2011/0041850 A1 | 2/2011 | Vandine et al. |
| 2011/0073112 A1 | 3/2011 | DiBlasi et al. |
| 2011/0092841 A1 | 4/2011 | Bassin |
| 2011/0100365 A1 | 5/2011 | Wedler et al. |
| 2011/0112424 A1 | 5/2011 | Kesselman et al. |
| 2011/0112425 A1 | 5/2011 | Muhlsteff et al. |
| 2011/0124982 A1 | 5/2011 | Pipke |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0205361 A1 | 8/2011 | Guillot et al. |
| 2011/0208081 A1 | 8/2011 | Smith et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0301481 A1 | 12/2011 | Heyer et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0152249 A1 | 6/2012 | Eger et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |

(56) References Cited

U.S. PATENT DOCUMENTS

| | | |
|---|---|---|
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0053840 A1 | 2/2014 | Liu |
| 2014/0066725 A1 | 3/2014 | Mulqueeny et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0345616 A1 | 11/2014 | Masic |
| 2014/0373845 A1 | 12/2014 | Dong |
| 2015/0034082 A1 | 2/2015 | Kimm et al. |
| 2015/0045687 A1 | 2/2015 | Nakai et al. |

FOREIGN PATENT DOCUMENTS

| | | |
|---|---|---|
| EP | 1005830 | 6/2000 |
| EP | 996358 | 1/2002 |
| EP | 1277435 | 1/2003 |
| WO | WO 2008/008659 | 1/2008 |
| WO | WO 2008/021222 | 2/2008 |
| WO | WO 2008/113752 | 9/2008 |
| WO | WO 2009/060330 | 5/2009 |

OTHER PUBLICATIONS

Speyer, J. L. et al., "Shiryayev sequential probability ratio test for redundancy management", Abstract, Journal of Guidance, Control, and Dynamics, vol. 7, No. 5 (1984), 1 page.

Chan, Steven et al., "A Sequential Probability Test for RAIM", Abstract, Proceedings of the 17th International Technical Meeting of the Satellite Division of The Institute of Navigation, (ION GNSS 2004), Long Beach, CA, Sep. 2004, 2 pgs.

Lai, Tze Leung, "Sequential Analysis: Some Classical Problems and New Challenges", Statistica Sinica, 11(2001), pp. 303-408.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Boitano, Louis J., "An Evaluation of Home Volume Ventilators That Support OpenCircuit Mouthpiece Ventilation", Respiratory Care, Nov. 2005, vol. 50, No. 11, pp. 1457-1461.

Heinrich, Rene et al., "Real-Time Computation of a Patient's Respiratory Effort During Ventilation", Journal of Clinical Monitoring and Computing (2006), 20: 193-200.

* cited by examiner

METHODS AND SYSTEMS FOR BREATH DELIVERY SYNCHRONIZATION

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios, such as mandatory ventilation modes and assist control ventilation modes.

Breath Delivery Synchronization

This disclosure describes systems and methods for providing novel systems and methods for trigging inspiration. In particular, this disclosure describes systems and methods for triggering ventilation utilizing a digital sample counting trigger mode.

In part, this disclosure describes a method for ventilating a patient with a ventilator. The method includes:

monitoring a physiological parameter of the patient based on one or more received sensor measurements;

calculating a first derivative and a second derivative of the physiological parameter for a first sample period;

selecting a first trigger count threshold and a first level based on the second derivative;

updating a sample count to form a first updated sample count for the first sample period based on first comparison results from at least one of the following:

comparing the first trigger count threshold to a previous trigger count threshold selected in a previous sample period, comparing the first derivative to a previous first derivative calculated for the previous sample period and comparing the second derivative to a previous second derivative calculated for the previous sample period, comparing an array of maxima of the second derivative to an array threshold, comparing the second derivative to the first level, and comparing a calculated first rate of change for the second derivative to a rate threshold;

comparing the first updated sample count to the first trigger count threshold; and triggering inspiration based on a first result of the comparing of the first updated sample count to the first trigger count threshold.

The disclosure further describes a ventilator system that includes: a pressure generating system, one or more sensors, a parameter module, a derivative module, a threshold module, a counter module, a compare module, and/or a trigger module. The pressure generating system generates a flow of breathing gas. The one or more sensors are operatively coupled to at least one of the pressure generating system, the patient, and a ventilation tubing system that delivers the flow of breathing gas from the pressure generating system to the patient. The one or more sensors generate sensor output for each sample period. The parameter module monitors a physiological parameter from the sensor output for each sample period. The derivative module calculates a first derivative and/or a second derivative for the physiological parameter for each sample period. The threshold module selects a trigger count threshold and a level based on the second derivative for each sample period. The counter module updates a sample count based on the first derivative, the second derivative, the level, and/or the trigger count threshold for each sample period to form an updated sample count. The compare module compares a selected trigger count threshold to an updated sample count for a same sample period. The trigger module triggers inspiration based on a receipt of a first result from the compare module.

The disclosure additionally describes a computer-readable medium having computer-executable instructions for performing a method for ventilating a patient with a ventilator. The method includes:

monitor an estimated patient effort of the patient based on received sensor measurements;

calculate a first derivative and a second derivative of the estimated patient effort for a first sample period;

select a first trigger count threshold and a first level based on the first derivative and the second derivative;

update a sample count to form a first updated sample count for the first sample period based on a comparison result from comparing the second derivative to the first level;

compare the first updated sample count to the first trigger count threshold; and trigger inspiration based on a first result from the comparing of the first updated sample count to the first trigger count threshold.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as in the drawings.

It is to be understood that both the foregoing general description and the following detailed description are explanatory and are intended to provide further explanation of the disclosure as claimed.

BRIEF DESCRIPTION OF THE DRAWINGS

The following drawing figures, which form a part of this application, are illustrative of embodiments of systems and methods described below and are not meant to limit the scope of the disclosure in any manner, which scope shall be based on the claims.

DETAILED DESCRIPTION

Figure 1:
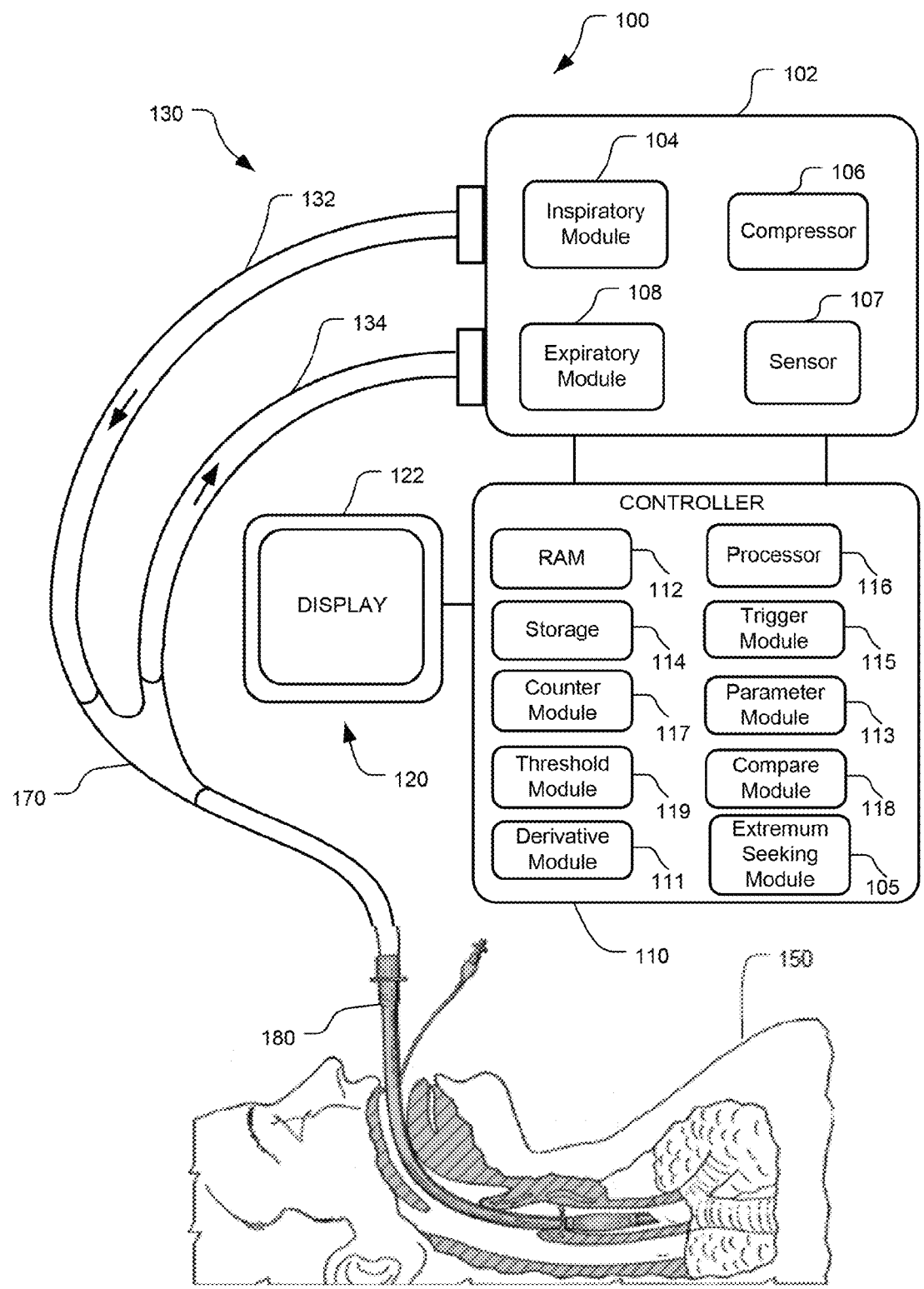
FIG. 1 illustrates an embodiment of a ventilator capable of running a digital sample counting trigger mode.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and flow rates. Ventilators capable of operating independently of external sources of pressurized air are also available.

As each patient may require a different ventilation strategy, modern ventilators can be customized for the particular needs of an individual patient. For example, several different ventilator modes, breath types, and/or settings have been created to provide better ventilation for patients in various different scenarios, such as mandatory ventilation modes and assist control ventilation modes. Assist control modes (also referred to herein as "spontaneous modes") allow a spontaneously breathing patient to trigger inspiration during ventilation. In a spontaneous mode of ventilation, the ventilator triggers inspiration upon the detection of patient demand to inhale and cycles or initiates expiration when a predetermined threshold is met or when a patient demand for exhalation is detected.

The response performance of a medical ventilator to a patient trigger from exhalation into inhalation and/or from inhalation into exhalation represents an important characteristic of a medical ventilator. A ventilator's inspiration trigger and/or exhalation cycle response impacts the patient's work of breathing and the overall patient-ventilator synchrony. The inspiration trigger and/or exhalation cycle response performance of a ventilator is a function of a patient's inspiratory behavior (breathing effort magnitude and timing characteristics) as well as the ventilator's gas delivery dynamics and flow control parameters (actuator response, dead bands, etc.).

Triggering delay time, cycling delay time, and asynchrony index are among key parameters that are used to measure the patient-ventilator synchrony. The asynchrony index is the ratio between the number of asynchronous event and the total respiratory rate. Miss-triggering is also considered as one of the factors that increases the patient-ventilator asynchrony index. Several different factors cause asynchrony events, such as variation in patient's breathing pattern, muscle strength, respiratory mechanics, ventilator performance, and ventilator characteristics.

In conventional flow triggering modes, a patient's inspiratory trigger is detected based on the magnitude of flow deviations generated by the patient's inspiratory effort. Recently, mechanical ventilator inspiration triggering and/or exhalation cycling improvements, such as triggering/cycling time delay reduction or ineffective breath detection have been developed. However, less attention has been paid to prevent undesired auto-triggered breath cycles caused by patient circuit vibrations or by humidification effects which agitate flow and pressure sensors/signals. Auto-triggering is more prevalent when a ventilator's triggering sensitivity value is set to a low value. One attempt to prevent auto-triggering is to change the triggering threshold until auto-triggering vanishes. However, a ventilator becomes less responsive to shallow breathes as the trigger threshold increases (the higher the trigger threshold, the larger a change in flow necessary to detect a patient trigger by the ventilator).

Further, missed inspiration triggering is particularly prevalent during the ventilation of chronic obstructive pulmonary disease patients (COPD). COPD patients demand another breath before they have fully exhaled. As a result, traditional flow triggering modes are not able to detect patient efforts even with the best optimized trigger thresholds.

Accordingly, the systems and methods described herein provide for an improved inspiration triggering and/or exhalation cycling. For example, improved inspiration triggering and/or exhalation cycling reduces or prevents auto-triggering even when the lowest trigger/cycle threshold is utilized. This new ventilator synchronization mechanism is referred to herein as the digital sample counting trigger mode ("DSCT mode"). While the DSCT mode is referred to herein as a mode, it may also be referred to as a triggering type, breath type, supplemental breath type, or supplemental mode because the DSCT mode is utilized in conjunction with or in addition to any spontaneous mode of ventilation running any suitable breath type for a spontaneous mode of ventilation. The DSCT mode improves ventilator synchrony by improving inspiration trigger and/or exhalation cycling detection. The DSCT mode detects weak patient efforts that could not have been previously detected by conventional flow inspiration triggering and/or exhalation cycling methods or systems. The DSCT mode utilizes the concavity theorem to characterize the data for each sample period to detect patient inspiration triggers and/or exhalation cycles. The concavity theorem can be expressed as follows:

If the function f is twice differentiable at x=c, then the graph of f is concave upward at (c, f(c)) if f"(c)>0 and concave downward if f" (c)<0.

The DSCT mode evaluates the signal of a derivative and/or second derivative of a physiological parameter for each sample period. If the signal of the physiological parameter meets one or more predetermine requirements for a predetermined number or count of consecutive sample periods, the DSCT mode detects a patient inspiration trigger and/or exhalation cycle. If the signal does not meet the one or more requirements, the count of sample periods is set to zero and the DSCT mode starts over and evaluates the signal from the physiological parameter for the next sample period.

The digital processing utilized by the DSCT mode provides for numerous advantages, such as fast detection, decreased asynchrony, and detection of patient conditions, such as COPD and ARDS. Conventional inspiration triggering and/or exhalation cycling modes, such as flow triggering, are all based on a continuous waveform crossing a predefined threshold, unlike the digital nature of the DSCT mode. The crossing of a continuous waveform may be very time consuming since the waveform must "continuously" decline below a preset trigger or cycle threshold regardless of when the patient initiated the trigger or cycle, unlike the sample counting of the DSCT mode. As such, conventional inspiration triggering and/or exhalation cycling modes require 300 ms or more to detect a patient trigger unlike the DSCT mode. The DSCT mode may detect a patient trigger and/or cycle in less than 70 milliseconds (ms) and in some embodiments, in 30 ms or less. Further, the DSCT mode prevents auto-triggers or auto-cycles from occurring by circuit noise even when the most sensitive triggering thresholds are utilized by the ventilator. Additionally, the DSCT mode can detect auto-positive end expiratory pressure (PEEP) before missing even one patient initiated inspiration trigger or exhalation cycle.

As such, the DSCT mode provides a way to detect digital samples (of any given measured or estimated pulmonary signal) that become dense or compressed in magnitude once the patient starts inhaling. Based on this detection, the ventilator delivers a breath once it identifies the acquired digital samples are compressed enough (in terms of magnitude) to be considered a patient effort or demand to inspire and/or exhale. Accordingly, the DSCT mode "characterizes" the compression/sparseness of digital samples taken from the estimated or measured patient pulmonary signal to detect the patient inhalation/exhalation demand to synchronize the mechanical ventilator breath delivery with patient inhalation/exhalation demand.

FIG. 1 illustrates a schematic diagram of an embodiment of an exemplary ventilator 100. The exemplary ventilator 100 illustrated in FIG. 1 is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106, accumulator and/or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 and/or through the inspiratory limb 132 according to prescribed ventilatory settings. The inspiratory module 104 is associated with and/or controls an inspiratory valve for controlling gas delivery to the patient 150 and/or gas delivery through the inspiratory limb 132. In some embodiments, inspiratory module 104 is configured to provide ventilation according to various ventilator modes, such as mandatory, spontaneous, and/or assist modes.

The expiratory module 108 is configured to release gases from the patient's lungs according to prescribed ventilatory settings. The expiratory module 108 is associated with and/or controls an expiratory valve for releasing gases from the patient 150.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1 illustrates a sensor 107 (e.g., flow sensor, pressure sensor, etc.) in pneumatic system 102.

Sensors 107 may communicate with various components of ventilator 100, e.g., pneumatic system 102, other sensors 107, expiratory module 108, inspiratory module 104, processor 116, controller 110, extremum seeking module 105, parameter module 113, derivative module 111, trigger module 115, counter module 117, compare module 118, threshold module 119, and any other suitable components and/or modules. A module as used herein refers to memory, one or more processors, storage, and/or other components of the type commonly found in command and control computing devices. In one embodiment, sensors 107 generate output and send this output to pneumatic system 102, other sensors 107, expiratory module 108, inspiratory module 104, processor 116, controller 110, extremum seeking module 105, parameter module 113, derivative module 111, trigger module 115, counter module 117, compare module 118, threshold module 119, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or expiratory triggering, for example. Sensors 107 may be placed in any suitable location, e.g., within the ventilatory circuitry or other devices communicatively coupled to the ventilator 100. For example, in some embodiments, one or more sensors 107 may be located in an accumulator. Further, sensors 107 may be placed in any suitable internal location, such as, within the ventilatory circuitry or within components or modules of ventilator 100. For example, sensors 107 may be coupled to the inspiratory and/or expiratory modules 104, 108 for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Any sensory device useful for monitoring changes in measurable parameters during ventilatory treatment may be employed in accordance with embodiments described herein. For example, in some embodiments, the one or more sensors 107 of the ventilator 100 include an inspiratory flow sensor and an expiratory flow sensor.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion or other known relationships from the monitored parameters.

The parameter module 113 monitors a physiological parameter of the patient for each sample period from sensor output from one or more sensors. The sample period as used herein refers to a discrete period of time in which the parameter module monitors a physiological parameter. In some embodiments, the sample period is a computation cycle for the ventilator 100. In some embodiments, the sample period is every 5 milliseconds (ms), 10 ms, 15 ms, 20 ms, 25 ms, or 30 ms. This list is exemplary only and is not meant to be limiting. Any suitable sample period for monitoring a physiological parameter of the patient may be utilized by the ventilator as would be understood by a person of skill in the art. In some embodiments, the parameter module 113 estimates and/or calculates the physiological parameter for monitoring based on the sensor output from one or more sensors. In other embodiments, parameter module 113 determines the physiological parameter for monitoring directly from the sensor output received from the one or more sensors. The physiological parameter may be any suitable physiological parameter for determining a patient initiated trigger as would be known by a person of skill in the art. In some embodiments, the physiological parameter is flow rate, net flow, rate of change in flow, pressure, rate of change in pressure, net pressure, patient effort or muscle pressure, estimated patient effort, estimated pressure, estimated flow, rate of change of patient effort, rate of change of estimated patient effort, and/or etc. This list is exemplary only and is not meant to be limiting.

In some embodiments, the parameter module 113 determines, calculates, and/or estimates the patient's inspiratory airway resistance, the expiratory airway resistance, the lung-thorax compliance, and the residual pressure. In some embodiments, the parameter module 113 estimates the patient's inspiratory airway resistance, the expiratory airway resistance, the lung-thorax compliance, and the residual pressure while the patient's respiratory muscles are fully relaxed, by fitting the measured flow onto the measured pressure at the mouth using a model of the patient's respiratory system. In additional embodiments, the parameter module 113 determines, estimates, or calculates the patient effort (also known as muscle pressure ($P_{mus}$)). In further embodiments, the parameter module 113 estimates the respiratory effort of the patient by utilizing a model of the respiratory system of the patient, the recursive least squares method, and the following estimated parameters: the patient's inspiratory airway resistance; the expiratory airway resistance; the lung-thorax compliance; and the residual pressure. In some embodiments, the parameter module 113 determines, estimates, and/or calculates a patient's flow rate, net flow, change in flow, pressure, change in pressure, net pressure, patient effort or muscle pressure directly from sensor output received from one or more sensors 107.

After determining the physiological parameter, the parameter module 113 may send the physiological parameter to any suitable component and/or module of the ventilator 100, such as the pneumatic system 102, expiratory module 108, inspiratory module 104, processor 116, controller 110, extremum seeking module 105, trigger module 115, counter module 117, compare module 118, derivative module 111, parameter module 113, and/or etc. In some embodiments, the parameter module 113 sends the physiological parameter to the derivative module 111.

The derivative module 111 calculates the first derivative ($D_X$ or $\dot{X}$) of the physiological parameter and/or calculates the second derivative ($D_{XX}$ or $\ddot{X}$) of the physiological parameter. In additional embodiments, the derivative module 111 amplifies the first derivative ($D_X$ or $\dot{X}$) and/or amplifies the second derivative ($D_{XX}$ or $\ddot{X}$) of the physiological parameter. "$D_X$," "$\dot{X}$," "$\ddot{X}$," and "$D_{XX}$" as utilized herein, can refer to the first and second derivatives and/or to the amplified first and second derivatives. In some embodiments, the derivative module 111 amplifies the first and second derivatives by an amplification factor of 5, 10, 20, 30, 40, 50, 60, 70, 80, and/or 90. This list is exemplary and is not meant to be limiting. Any suitable amplification factor may be utilized by the ventilator as would be known by a person of skill in the art. However, different amplification factors require different predetermined requirements and/or thresholds to be utilized during the DSCT mode. In additional embodiments, the first derivative is amplified by 50 and the second derivative is amplified by 10. In other embodiments, both the first derivative and the second derivative are amplified by 10.

In some embodiments, the derivative module 111 calculates the first and/or second derivative utilizing the following equations:

$$\dot{X}(i)=X(i)-X(i-1); \text{ and}$$

$$\ddot{X}(i)=\dot{X}(i)-\dot{X}(i-1),$$

wherein $\dot{X}$ is an amplified first derivative of a physiological parameter, $\ddot{X}$ is an amplified second derivative of the physiological parameter, i is an index that represents the state of the digital sampled signal, and X is the physiological parameter. In some embodiments the physiological parameter is directly measured and in other embodiments the physiological parameter is estimated by the derivative module 111 of the ventilator 100.

The derivative module 111 may send the first derivative, second derivative, and/or amplified first and second derivatives to other ventilator components, such as the pneumatic system 102, expiratory module 108, inspiratory module 104, processor 116, controller 110, extremum seeking module 105, trigger module 115, counter module 117, compare module 118, threshold module 119, parameter module 113, derivative module 111, and/or any other suitable components and/or modules of the ventilator 100. In some embodiments, the derivative module 111 may send the first and second derivatives or the amplified first and second derivatives to the counter module 117 and the trigger module 115.

The extremum seeking module 105 determines or finds maxima (peaks) and/or minima (valleys) of the first derivative and/or the second derivative. In some embodiments, the extremum seeking module 105 utilizes the extremum seeking algorithm to determine maxima and/or minima of the first derivative and/or second derivative. In some embodiments, the extremum seeking module 105 finds the maxima and/or the minima of the first derivative and/or the second derivative in real time. Further, the extremum seeking module 105 may keep the last maximum found for the first derivative and may buffer the maxima found on the second derivative during the exhalation phase. The extremum seeking module 105 may then keep track if the last extremum point found for the second derivative is a minimum or a maximum. Further, a predetermined number of the peaks (or maxima) of the second derivative are dynamically buffered to form an array of the second derivative maxima ($D_{XX_{MAX}}$ or $D_{\ddot{x}_{Max}}$). In some embodiments, the array of the second derivative maxima includes the last or previous three peaks (or maxima) of the second derivative.

The extremum seeking module 105 may send the maxima and/or minima of the first and/or second derivative and/or the array of the second derivative maxima to other ventilator components, such as the pneumatic system 102, expiratory module 108, inspiratory module 104, processor 116, controller 110, trigger module 115, counter module 117, compare module 118, threshold module 119, parameter module 113, derivative module 111, and/or any other suitable components and/or modules of the ventilator 100.

The pneumatic system 102 may include a variety of other components, including mixing modules, valves, tubing, accumulators, filters, etc. Controller 110 is operatively coupled with pneumatic system 102, signal measurement and acquisition systems (e.g., sensor(s) 107, parameter module 113, and/or derivative module 111), and an operator interface 120 that may enable an operator to interact with the ventilator 100 (e.g., change ventilator settings, select operational modes, view monitored parameters, etc.).

In some embodiments, the operator interface 120 of the ventilator 100 includes a display 122 communicatively coupled to ventilator 100. Display 122 may provide various input screens, for receiving clinician input, and various display screens, for presenting useful information to the clinician. In embodiments, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 illustrates a trigger count threshold, a sample count, a level, a rate threshold, a ratio threshold, the predetermined requirements, a physiological parameter, a graph or waveform of the physiological parameter, a detected patient trigger, a counted sample, and/or any other information known, received, or stored by the ventilator 100.

In some embodiments, controller 110 includes memory 112, one or more processors 116, storage 114, and/or other components of the type commonly found in command and control computing devices. Controller 110 may further include a derivative module 111, a parameter module 113, a trigger module 115, a counter module 117, a compare module 118, and a threshold module 119 as illustrated in FIG. 1. In alternative embodiments, the derivative module 111, the parameter module 113, the trigger module 115, the counter module 117, the compare module 118, and the threshold module 119 are located in other components of the ventilator 100, such as in the pressure generating system 102 (also known as the pneumatic system 102) or inspiratory module 104.

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The threshold module 119 selects a trigger count threshold and a level based on the second derivative and/or the first derivative for each sample period. The threshold module 119 may receive the second derivative for each sample period from the derivative module 111. In some embodiments, the second derivative received by the threshold module 119 has been amplified by the derivative module 111. In other embodiments, the threshold module 119 receives the second derivative for each sample period from any suitable module or component of the ventilator 100.

In some embodiments, the threshold module 119 selects between a large (also referred to herein as rigid) and a small (also referred to herein as relaxed) trigger count threshold. The large trigger count threshold requires a larger number or a larger count of sample periods to meet a set of predetermined requirements before a trigger is detected than a small trigger count threshold requires. As such, the large trigger count threshold is a rigid threshold that requires more time to detect a patient trigger than the small trigger count threshold that takes less time to detect a patient trigger. For example, in some embodiments, the trigger count threshold is selected from one of the following groups of a large and a small trigger count threshold: 1 and 2; 1 and 3; 2 and 3; 2 and 4; 3 and 4; 3 and 6; 4 and 5; and 4 and 6. This list is not limiting. Any suitable group of a large and a small trigger count threshold may be utilized by the threshold module 119 as would be understood by a person of skill in the art. In some embodiments, the trigger count threshold is selected from a large and a small trigger count threshold of 2 and 4. In other embodiments, the trigger count threshold is selected from a large and a small trigger count threshold of 1 and 2.

In further embodiments, the threshold module 119 selects between a large and a small level. The large level requires a less negative second derivative to be present to detect a patient trigger than a small level requires. As such, the large level is a relaxed threshold because the second derivative has to be larger (or less negative) to detect a patient trigger than the small level threshold that requires a smaller (or more negative) patient derivative to detect a patient trigger. For example, in some embodiments, the level is selected from one of the following groups of a large and a small level: −3 and −8; −4 and −9; −5 and −10; −10 and −15; and −15 and −20. This list is not limiting. Any suitable group of a large and a small level may be utilized by the threshold module 119 as would be understood by a person of skill in the art. In some embodiments, the level is selected from a large level of −3 and a small level of −8.

The threshold module 119 determines a signal to noise ratio for the second derivative. The threshold module 119 compares the signal to noise ratio to a threshold ratio. If the threshold module 119 determines that the signal to noise ratio is greater than the ratio threshold based on the comparison, the threshold module 119 selects a small trigger count threshold and/or selects a large level. A small trigger count threshold and a large level allows the ventilator 100 running a DSCT mode to detect a patient trigger in a shorter amount of time and with less of a decrease in the physiological parameter than the selection of a large trigger count threshold and a small level. If the threshold module 119 determines that the signal to noise ratio is less than or equal to the ratio threshold based on the comparison, the threshold module 119 selects a large trigger count threshold and/or selects a small level. The selection of a large trigger count threshold and a small level by the threshold module 119 requires a longer amount of time and a larger decrease in the physiological parameter to detect a patient trigger by the ventilator 100 running a DSCT mode. In some embodiments, the ratio threshold is less than zero or less than −1. This list is exemplary only and is not meant to be limiting. Any suitable ratio threshold may be utilized by the ventilator 100 as would be known by a person of skill in the art. Further, the ratio may need to be adjusted based on age, weight, height, gender, ideal body weight, and/or disease state.

In some embodiments, the threshold module 119 sends the selected trigger count threshold and/or the selected level to any component and/or module of the ventilator 100, such as the pneumatic system 102, expiratory module 108, inspiratory module 104, processor 116, controller 110, extremum seeking module 105, trigger module 115, counter module 117, compare module 118, derivative module 111, parameter module 113, and/or etc. In some embodiments, the threshold module 119 sends the selected trigger count threshold to the counter module 117, the compare module 118 and/or the trigger module 115. In further embodiments, the threshold module 119 sends the selected level to the counter module 117.

The counter module 117 updates a sample count based on one or more of the first derivative, the second derivative, the level, and the trigger count threshold for each sample period to form an updated sample count. As such, the counter module 117 updates the sample count based on whether one or more predetermined requirements relating to the first derivative, the second derivative, the level, and the trigger count threshold have been met for each sample period. The list of predetermined requirements provided below is exemplary and is not meant to be limiting. As known by a person of skill in the art, any suitable predetermined requirement may be checked by the counter module 117 in order to determine whether or not to count a given sample period or to determine how to update a sample count for a giving sample period.

In some embodiments, the counter module 117 compares the selected trigger count threshold received from the threshold module 119 to the trigger count threshold received from the threshold module 119 for the previous sample period. The previous sample period is the sample period that occurred immediately before the current sample period or is the sample period currently being evaluated by the counter module 117. If the counter module 117 determines that the current trigger count threshold is not the same as the previous trigger count threshold, the counter module 117 updates the sample count to zero. In some embodiments, if the counter module 117 determines that the current trigger count threshold is the same as or is equivalent to the previous trigger count threshold, the counter module 117 updates the sample count (n) to n+1. In alternative embodiments, if the counter module 117 determines that the current trigger count threshold is the same as or is equivalent to the previous trigger count threshold, the counter module 117 checks one or more additional requirements before updating the sample count. In some embodiments, during an initial sample period (e.g., the first sample period of the DSCT mode run by the ventilator 100) when no previous sample period data exists, the counter module 117 automatically determines that the current trigger count threshold is not equivalent to the previous trigger count threshold. In alternative embodiments, during an initial sample period when no previous sample period data exists, the counter module 117 automatically determines that the current trigger count threshold is equivalent to the previous trigger count threshold or skips performing this requirement check altogether.

In some embodiments, the counter module 117 compares the first derivative calculated for the current sample period to a previous first derivative calculated during a pervious sample period. The counter module 117 may receive the current first derivative and the pervious second derivative from the derivative module 111. In some embodiments, the counter module 117 may receive the first and second derivatives from any suitable component or module of the ventilator 100. In further embodiments, the first and second derivatives are amplified.

If the counter module 117 determines that first derivative is equal to or more than the previous first derivative, the counter module 117 updates the sample count (n) to zero. In some embodiments, if the counter module 117 determines that first derivative is less than the previous first derivative, the counter module 117 updates the sample count (n) to n+1. In alternative embodiments, if the counter module 117 determines that first derivative is less than the previous first derivative, the counter module 117 checks one or more additional requirements before updating the sample count. In some embodiments, during an initial sample period (e.g., the first sample period of the DSCT mode run by the ventilator 100) when no previous sample period data exists, the counter module 117 automatically determines that the current first derivative is not less than the first derivative. In alternative embodiments, during an initial sample period when no previous sample period data exists, the counter module 117 automatically determines that the current first derivative is equal to or greater than the previous first derivative or skips performing this requirement check altogether.

In some embodiments, the counter module 117 compares the second derivative calculated for the current sample period to a previous second derivative calculate during a pervious sample period. The counter module may receive the current second derivative and the pervious second derivative from the derivative module 111.

If the counter module 117 determines that second derivative is equal to or more than the previous second derivative, the counter module 117 updates the sample count (n) to zero. In some embodiments, if the counter module 117 determines that second derivative is less than the previous second derivative, the counter module 117 updates the sample count (n) to n+1. In alternative embodiments, if the counter module 117 determines that second derivative is less than the previous second derivative, the counter module 117 checks one or more additional requirements before updating the sample count. In some embodiments, during an initial sample period (e.g., the second sample period of the DSCT mode run by the ventilator 100) when no previous sample period data exists, the counter module 117 automatically determines that the current second derivative is not less than the second derivative. In alternative embodiments, during an initial sample period when no previous sample period data exists, the counter module 117 automatically determines that the current first derivative is equal to or greater than the previous first derivative or skips performing this requirement check altogether.

In additional embodiments, the counter module 117 compares the array of maxima of the second derivative ($D_{XX_{MAX}}$ or $D_{\ddot{X}_{Max}}$) to an array threshold ($\psi$). The array threshold may be determined by the ventilator or selected or input by the operator. In some embodiments, the array threshold is 70 cm of $H_2O$ per second, 60 cm of $H_2O$ per second, 50 cm of $H_2O$ per second, 40 cm of $H_2O$ per second, or 30 cm of $H_2O$ per second. If the counter module 117 determines that the array of maxima of the second derivative is more than or equal to the array threshold, the counter module 117 updates the sample count (n) to zero. In some embodiments, if the counter module 117 determines that the array of maxima of the second derivative is less than the array threshold, the counter module 117 updates the sample count (n) to n+1. In alternative embodiments, if the counter module 117 determines that the array of maxima of the second derivative is less than the array threshold, the counter module 117 checks one or more additional requirements before updating the sample count. The use of the array threshold as a predetermined requirement prevents or reduces auto triggering (also referred to as false triggering) caused by patient circuit vibration and/or noise.

In further embodiments, the counter module 117 compares the second derivative to the selected level for the current sample period. As discussed above, the second derivative may be an amplified second derivative. The counter module 117 may receive the selected level from the threshold module 119 and the second derivative from the derivative module 111. If the counter module 117 determines that second derivative is more than the level, the counter module 117 updates the sample count (n) to zero. In some embodiments, if the counter module 117 determines that second derivative is less than or equal to the level, the counter module 117 updates the sample count (n) to n+1. In alternative embodiments, if the counter module 117 determines that second derivative is less than or equal to the level, the counter module 117 checks one or more additional requirements before updating the sample count.

In additional embodiments, the counter module 117 compares a rate of change for the second derivative to a rate threshold. The counter module 117 and/or the parameter module 113 may calculate or determine the rate of change of the second derivative based on the current and one or more previous second derivatives. As such, in some embodiments, the counter module 117 receives the rate of change for the second derivative from the parameter module 113.

If the counter module 117 determines that rate of change is equal to or more than the rate threshold, the counter module 117 updates the sample count (n) to zero. In some embodiments, if the counter module 117 determines that the rate of change is less than the rate threshold, the counter module 117 updates the sample count (n) to n+1. In alternative embodiments, if the counter module 117 determines that the rate of change is less than the rate threshold, the counter module 117 checks one or more additional requirements before updating the sample count. In some embodiments, during an initial sample period (e.g., the second sample period of the DSCT mode run by the ventilator 100) when no previous sample period data exists, the counter module 117 automatically determines that the rate of change is equal to or more than the rate threshold. In alternative embodiments, during an initial sample period when no previous sample period data exists, the counter module 117 automatically determines that the rate of change is less than the rate threshold or skips performing this requirement check altogether.

The rate threshold may be input or selected by the clinician. In other embodiments, the rate threshold is automatically selected by the ventilator based on one or more patient parameters (e.g., ideal body weight, height, weight, age, disease condition, and/or etc.) and/or physiological parameters (e.g., flow, pressure, tidal volume, heart rate, and/or etc.). In some embodiments, the rate threshold is the Lipschitz constant. In some embodiments, the rate threshold is less than 70 cm of $H_2O$ per second, 60 cm of $H_2O$ per second, 50 cm of $H_2O$ per second, 40 cm of $H_2O$ per second, or 30 cm of $H_2O$ per second. This list is exemplary only and is not meant to be limiting. Any suitable rate threshold may be utilized by the ventilator 100 as would be known by a person of skill in the art. Further, the ratio may need to be adjusted based on the patient's parameters, such as age, weight, height, gender, ideal body weight, and/or disease state.

In some embodiments, the counter module 117 updates the sample count to n+1 only when all of the predetermined requirements discussed above (e.g., the trigger count threshold is equivalent to the previous trigger count threshold, the first derivative is less than the previous first derivative, the second derivative is less than the previous second derivative, the second derivative is less than or equal to the level, and the second derivative's rate of change is not too large) for the counter module 117 are met. In other embodiments, the counter module 117 updates the sample count to n+1 when a select combination of the predetermined requirements listed above is met. In additional embodiments, the counter module 117 updates the sample count to zero when any one of the predetermined requirements discussed above for the counter module 117 are not met. In other embodiments, the counter module 117 updates the sample count to zero when a select combination of the predetermined requirements listed above are not met.

The counter module 117 may send the updated sample count to any suitable component or module of the ventilator 100, such as the pneumatic system 102, expiratory module 108, inspiratory module 104, processor 116, controller 110, extremum seeking module 105, trigger module 115, threshold module 119, compare module 118, parameter module 113, derivative module 111, and/or etc. In some embodiments, the counter module 117 sends the updated sample count to the compare module 118.

The compare module 118 compares a selected trigger count threshold to an updated sample count for a same sample period. The compare module 118 may receive the selected trigger count threshold and the updated sample count from any suitable ventilator module or component, such as the pneumatic system 102, extremum seeking module 105, expiratory module 108, inspiratory module 104, processor 116, controller 110, trigger module 115, threshold module 119, counter module 117, parameter module 113, derivative module 111, and/or etc. In some embodiments, the compare module 118 receives the selected trigger count threshold from the threshold module 119 and receives the updated sample count from the counter module 117. If the compare module 118 determines that the updated sample count is not equal to the selected trigger count threshold, then the compare module 118 waits for the next updated sample count and the next selected trigger count threshold for the next sample period. The next sample period is the sample period immediately following the current sample period. Further, in some embodiments, if the compare module 118 determines that the updated sample count is not equal to the selected trigger count threshold, the compare module 118 does not send any information to the trigger module 115. In other embodiments, if the compare module 118 determines that the updated sample count is not equal to the selected trigger count threshold, the compare module 118 sends a second result to the trigger module 115. The second result may be instructions and/or a command to not trigger inspiration or to continue exhalation. In other embodiments, the second results may be a notification that the updated sample count is not equal to the selected trigger count threshold. If the compare module 118 determines that the updated sample count is equal to the selected trigger count threshold, the compare module 118 may send a first result to the trigger module 115. The first result may be instructions and/or a command to trigger inspiration and/or to end expiration. In alternative embodiments, the first result may be a notification that the updated sample count is equal to the selected trigger count threshold. In other embodiments, the compare module 118 sends the first or second result to any suitable component or module of the ventilator 100, such as the pneumatic system 102, expiratory module 108, inspiratory module 104, processor 116, controller 110, extremum seeking module 105, trigger module 115, threshold module 119, counter module 117, parameter module 113, derivative module 111, and/or etc.

Ventilators 100, depending on their mode of operation, may trigger automatically and/or in response to a detected change in a ventilator 100 and/or physiological parameter. The trigger module 115 triggers inspiration based on a receipt of a first result. In some embodiments, the first result is received by the trigger module 115 from the compare module 118. In alternative embodiments, the first result is received by the trigger module 115 from another component or module of the ventilator 100.

To prevent apnea in the event that a patient trigger is not detected by the DSCT mode of the ventilator 100, the trigger module 115 also triggers inspiration after a predetermined amount exhalation time. Accordingly, the predetermined amount of exhalation time is also known as an apnea interval in some ventilators. For example, the trigger module 115 will automatically trigger an inspiration after 20 seconds, 30 seconds, or 60 seconds of exhalation time. In some embodiments, the predetermined amount of time is determined by the clinician and/or ventilator 100 based on whether the patient 150 is an infant, child, adult, male, female, and/or suffering from a specific disease state.

The trigger module 115 triggers inspiration by sending instructions and/or a command to a pneumatic system 102, an expiratory module 108, an inspiratory module 104, a processor 116, and/or a controller 110. The instructions and/or commands cause the one or more ventilator components and/or modules to change the delivered flow and/or pressure and to adjust the valves as needed to trigger inspiration.

In some embodiments, the trigger module 115 receives a second result. In some embodiments, the second result is received by the trigger module 115 from the compare module 118. In alternative embodiments, the second result is received by the trigger module 115 from another component or module of the ventilator 100. In some embodiments, if the trigger module 115 receives a second result, the trigger module 115 continues to deliver exhalation until the trigger module 115 receives a first result from another sample period.

The trigger module 115 delivers exhalation by sending instructions and/or a command to a pneumatic system 102, an expiratory module 108, an inspiratory module 104, a processor 116, and/or a controller 110. The instructions and/or commands cause the one or more ventilator components and/or modules to change the delivered flow and/or pressure and to adjust the valves as needed to deliver exhalation.

The ventilator 100 and its modules discussed above as illustrated in FIG. 1 are capable of performing the DSCT mode. While the description of the ventilator's capability to perform the DSCT mode above is directed to triggering, the ventilator 100 and its modules are also capable of utilizing the DSCT mode similarly for cycling. For example, the DSCT mode detects cycling by detecting when a predetermined number of digital samples become almost equal and flat in their magnitude (on a plateau waveform) at the end of inhalation. In these embodiments, the trigger module 115 of the ventilation 100 triggers exhalation or cycles inspiration to exhalation.

Figure 10:
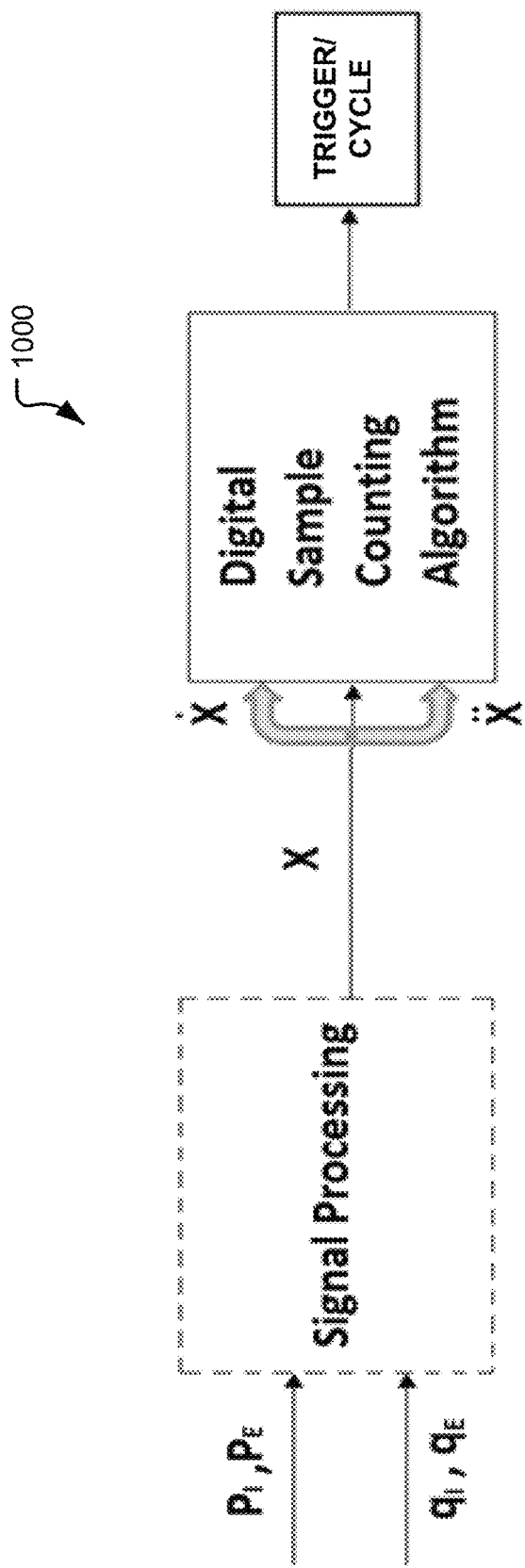
FIG. 10 illustrates an embodiment of a schematic of the digital sample counting trigger mode.

FIG. 10 illustrates an embodiment of a high level diagram or schematic of the DSCT mode 1000. As illustrated, inspiration pressure ($P_I$), expiration pressure ($P_E$), inspiration flow ($q_I$), and expiration flow ($q_E$) undergo signal processing. In the schematic of the DSCT mode 1000, during signal processing, the first derivative ($\dot{X}$) and the second derivative ($\ddot{X}$) of the physiological parameter are determined for each sample period. In some embodiments, the signal processing estimates the derivative of muscle pressure (an estimated input) for input into the digital sample counting algorithm. In other embodiments, the signal processing utilizes net flow (a direct measurement) for input into the digital sample counting algorithm. Next, the first and second derivatives are evaluated by the digital sample counting algorithm. The digital sample counting algorithm determines whether to count a sample period based at least on the first derivative and/or second derivative of that sample period and then triggers and/or cycles when a predetermined number sample periods are counted by the digital sample counting algorithm.

Figure 2:
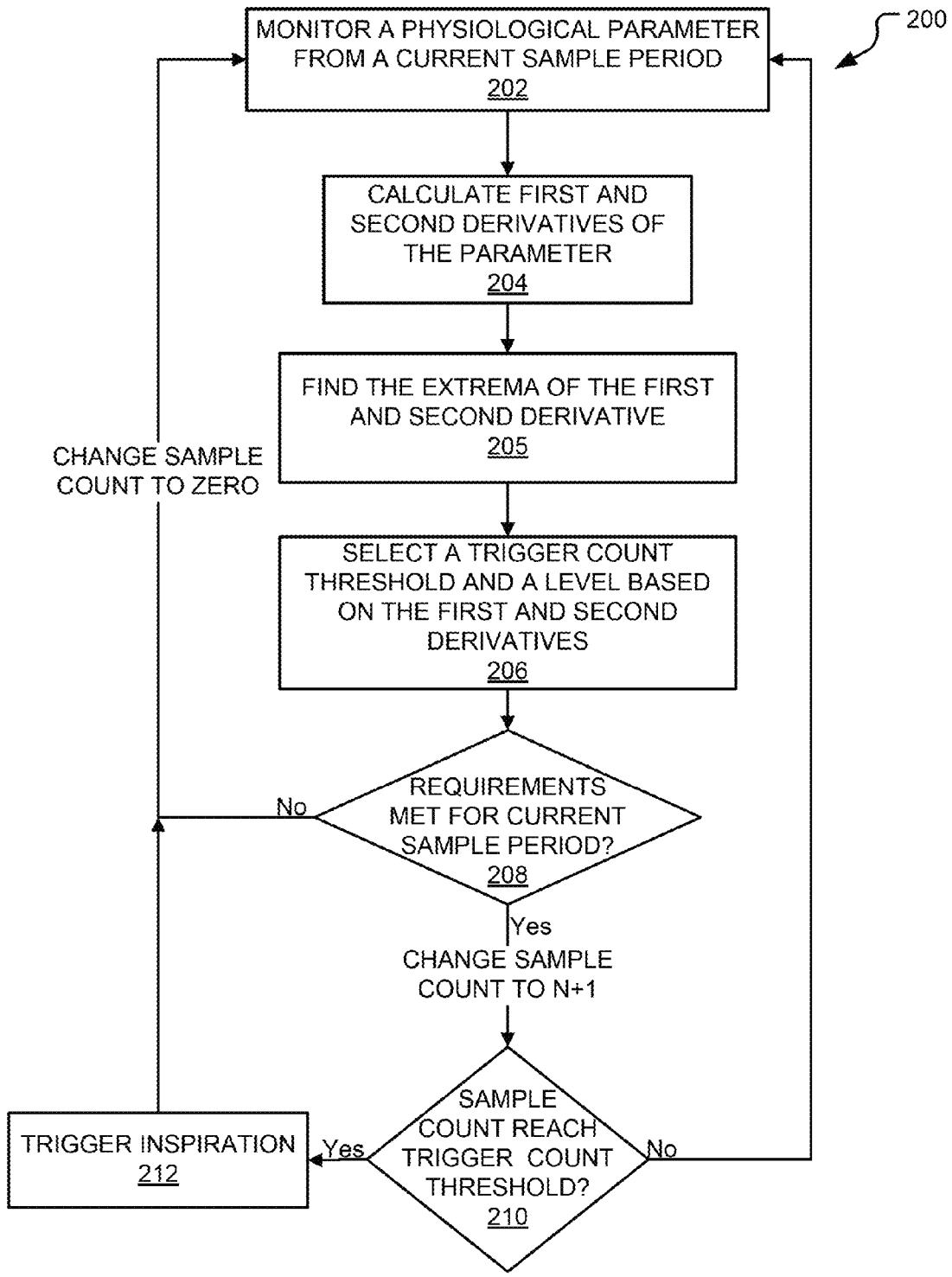
FIG. 2 illustrates an embodiment of a method for synchronizing ventilation with breath demand of a patient on a ventilator.

FIG. 2 illustrates an embodiment of a method 200 for synchronizing ventilation with the breath demand of a patient on a ventilator. In some embodiments, method 200 is performed by the ventilator to execute a DSCT mode. Method 200 begins at the start of exhalation. As illustrated, method 200 includes a monitoring operation 202. During the monitoring operation 202, the ventilator monitors a physiological parameter of the patient based on one or more received sensor measurements. In some embodiments, the ventilator during monitoring operation 202 estimates and/or calculates the physiological parameter for monitoring based on the sensor measurements from one or more sensors. In other embodiments, the ventilator during monitoring operation 202 determines the physiological parameter for monitoring directly from the sensor measurements received from the one or more sensors.

In some embodiments, the ventilator during monitoring operation 202 determines, calculates, and/or estimates the patient's inspiratory airway resistance, the expiratory airway resistance, the lung-thorax compliance, and the residual pressure. In some embodiments, the ventilator during monitoring operation 202 estimates the patient's inspiratory airway resistance, the expiratory airway resistance, the lung-thorax compliance, and the residual pressure while the patient's respiratory muscles are fully relaxed, by fitting the measured flow onto the measured pressure at the mouth using a model of the patient's respiratory system. In additional embodiments, the ventilator during monitoring operation 202 estimates or calculates the patient effort (also known as muscle pressure ($P_{mus}$)) or the rate of change of the patient effort ($\dot{P}_{mus}$). In further embodiments, the ventilator during monitoring operation 202 estimates the respiratory effort of the patient by utilizing a model of the respiratory system of the patient, the recursive least squares method, and the following estimated parameters: the patient's inspiratory airway resistance; the expiratory airway resistance; the lung-thorax compliance; and the residual pressure. In some embodiments, the ventilator during monitoring operation 202 determines, estimates, and/or calculates a patient's flow rate, net flow, change in flow, pressure, change in pressure, net pressure, patient effort or muscle pressure from one or more sensor measurements. The monitoring operations 202 may be performed by inspiration module, processor, controller, pneumatic system, exhalation module, sensors, and/or parameter module of the ventilator.

Figure 3:
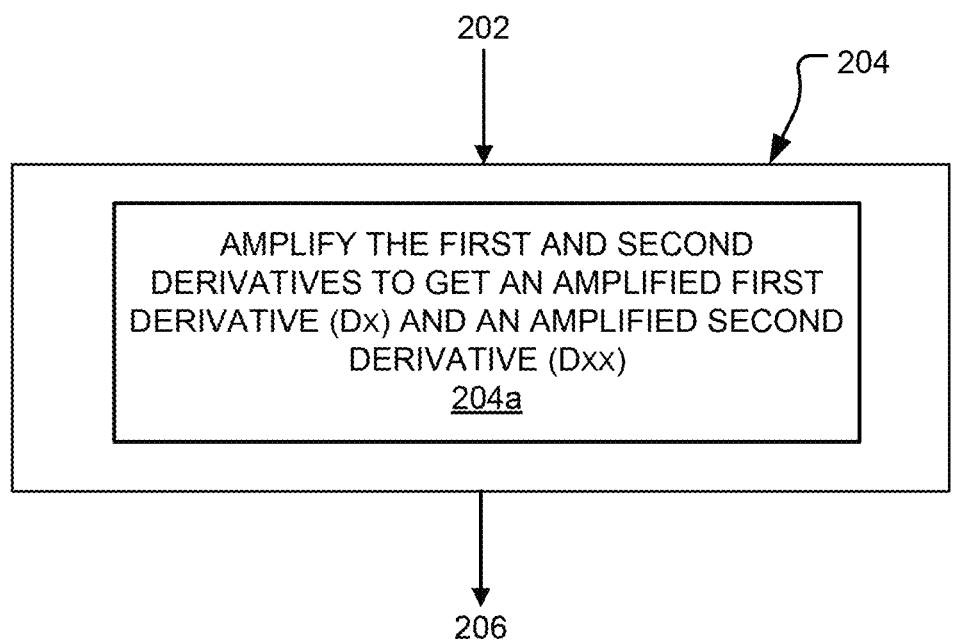
FIG. 3 illustrates an embodiment of a portion of the method for synchronizing ventilation with breath demand illustrated in FIG. 2.

Method 200 also includes a calculating operation 204. The ventilator during the calculating operation 204 calculates the first and/or second derivative of the physiological parameter for each sample period. In some embodiments, the ventilator during the calculating operation 204 performs an amplification operation 204a, as illustrated in FIG. 3. The ventilator during the amplification operation 204a of the calculating operation 204 amplifies the first and/or the second derivative of the physiological parameter. In some embodiments, the ventilator during the amplification operation 204a of the calculating operation 204 amplifies the first and/or second derivative by 5, 10, 20, 30, 40, 50, 60, 70, 80, and/or 90. This list is exemplary and is not meant to be limiting. Any suitable amplification factor may be utilized by the ventilator as would be known by a person of skill in the art. In other embodiments, the ventilator during the amplification operation 204a of the calculating operation 204 amplifies the first derivative by an amplification factor of 50 and amplifies the second derivative by an amplification factor of 10. In alternative embodiments, the ventilator during the amplification operation 204a of the calculating operation 204 amplifies both the first derivative and the second derivative by an amplification factor of 10.

In some embodiments, the physiological parameter is an estimated patient effort and the ventilator during the calculating operation 204 calculates first and second derivatives of the estimated patient effort. In further embodiments, the ventilator during the calculating operation 204 amplifies the first and second derivatives of the estimated patient effort. The calculating operations 204 may be performed by the inspiration module, processor, controller, pneumatic system, exhalation module, parameter module, sensors, and/or derivative module of the ventilator. In some embodiments, the ventilator during calculating operation 204 calculates the first and/or second derivative utilizing the following equations:

$$\dot{X}(i) = X(i) - X(i-1); \text{ and}$$

$$\ddot{X}(i) = \dot{X}(i) - \dot{X}(i-1),$$

wherein $\dot{X}$ is an amplified first derivative of a physiological parameter, $\ddot{X}$ is an amplified second derivative of the physiological parameter, i is an index that represents the state of the digital sampled signal, and X is the physiological parameter.

Method 200 also includes an extremum seeking operation 205. The ventilator during the extremum seeking operation 205 finds or determines maxima and/or minima of the first derivative and/or the second derivative. In some embodiments, the ventilator during the extremum seeking operation 205 determines maxima and/or the minima of the first derivative and/or the second derivative in real time and/or utilizes an extremum seeking algorithm. In further embodiments, the ventilator during the extremum operation 205 keeps the last maximum found for the first derivative and buffers the maxima found on the second derivative during the exhalation phase. The extremum seeking operation 205 may then keep track if the last extremum point found for the second derivative is a minimum or a maximum. In additional embodiments, a predetermined number of the peaks (or maxima) of the second derivative are dynamically buffered to form an array of the second derivative maxima ($D_{XX_{MAX}}$ or $D_{\ddot{X}_{Max}}$) by the ventilator during the extremum seeking operation 205. In some embodiments, the array of the second derivative maxima includes the last or previous three peaks of the second derivative.

Figure 4:
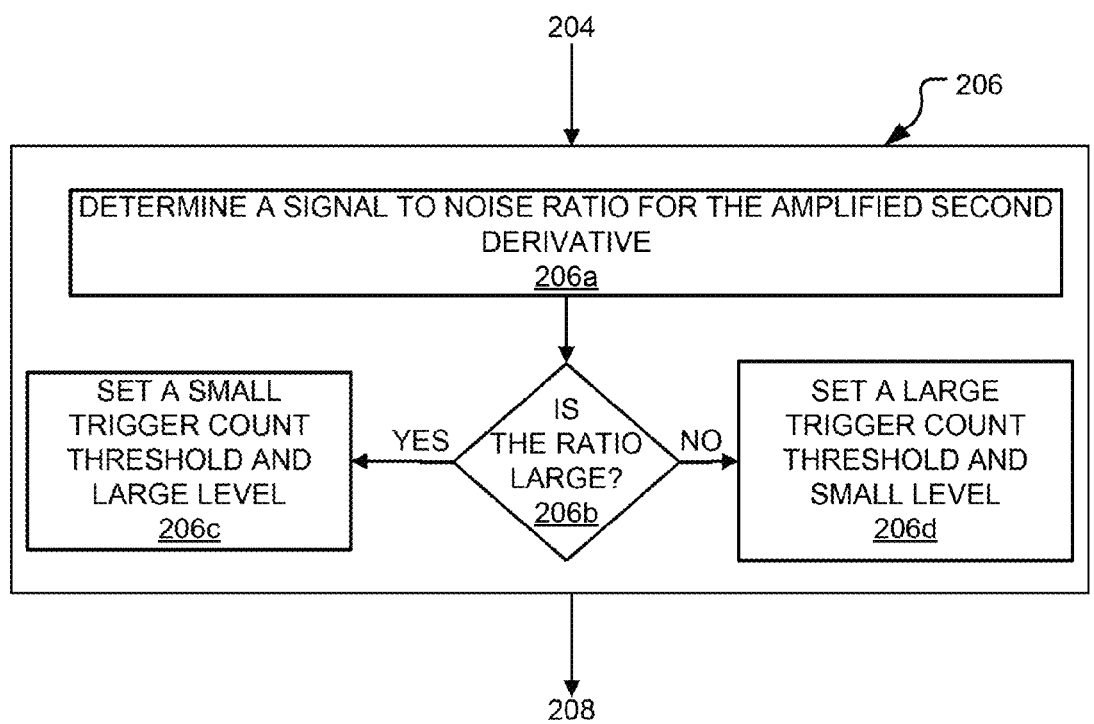
FIG. 4 illustrates an embodiment of a portion of the method for synchronizing ventilation with breath demand illustrated in FIG. 2.
Figure 5:
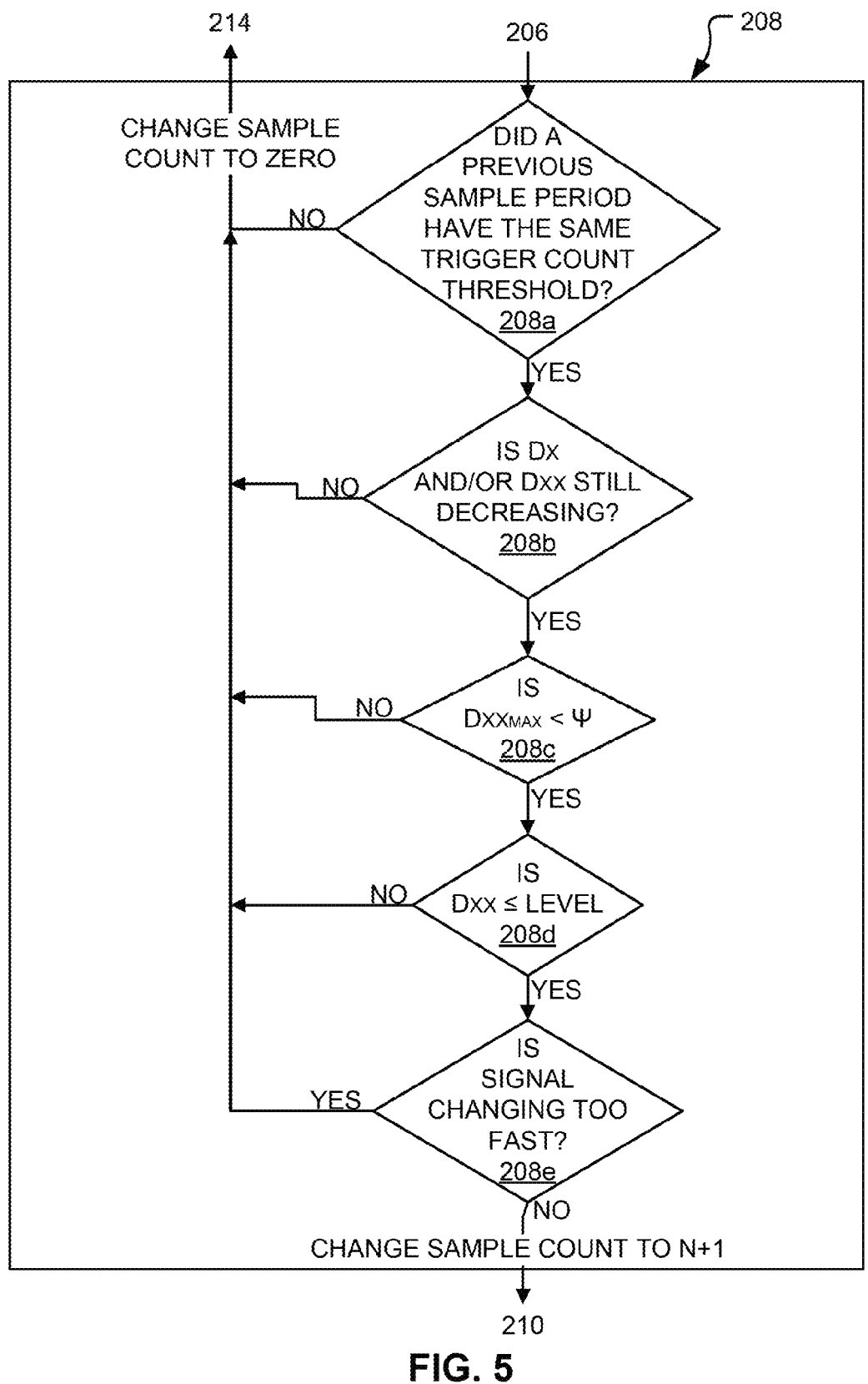
FIG. 5 illustrates an embodiment of a portion of the method for synchronizing ventilation with breath demand illustrated in FIG. 2.

Further, method 200 includes a selecting operation 206. The ventilator during the selecting operation 206 selects a trigger count threshold and/or a level based on the first derivative and/or the second derivative and/or their respective signals. In some embodiments, the selecting operation 206 includes a signal to noise operation 206a, a ratio determining operation 206b, a relaxed setting operation 206c, and/or a rigid setting operation 206d, as illustrated in FIG. 4. In some embodiments, the ventilator during a signal to noise operation 206a determines a signal to noise ratio of the second derivative and during a ratio determining operation 206b compares the signal to noise ratio of the second derivative to a ratio threshold. In these embodiments, if the ventilator during the ratio determining operation 206b determines that the signal to noise ratio for the second derivative is greater than the ratio threshold, the ventilator selects to perform relaxed setting operation 206c. The ventilator during the relaxed setting operation 206c selects a small trigger count threshold for the first trigger count threshold and/or selects a large level for the first level. In these embodiments, if the ventilator during the ratio determining operation 206b determines that the signal to noise ratio for the second derivative is less than or equal to the ratio threshold, the ventilator selects to perform a rigid setting operation 206d. The ventilator during the rigid setting operation 206d selects a large trigger count threshold for the first trigger count threshold and/or selects a small level for the first level. In some embodiments, the second derivative has been amplified.

In some embodiments, the ventilator during the ratio determining operation 206b selects between a large and a small level. The large level requires a less negative second derivative to be present to detect a patient trigger than a small level requires. As such, the large level is a relaxed threshold because the descending second derivative can be larger (or less negative) to detect a patient trigger than the small level threshold.

In some embodiments, the ventilator during the ratio determining operation 206b selects between a large and a small trigger count threshold. The large trigger count threshold requires a larger number or a larger count of sample periods to meet a set of predetermined requirements before a trigger is detected by a ventilator performing method 200 than a small trigger count threshold requires. As such, the large trigger count threshold is a rigid threshold that causes the ventilator performing method 200 to require more time to detect a patient trigger than required by the ventilator when the small trigger count threshold is selected.

The selecting operations 206 may be performed by the inspiration module, processor, controller, pneumatic system, exhalation module, parameter module, sensors, derivative module and/or threshold module of the ventilator.

Additionally, method 200 includes an updating operation 208. During updating operation 208, the ventilator updates a sample count to form an updated sample count for each sample period based on one or more comparison results for each sample period. The one or more comparison results are a determination of whether or not one or more predetermined requirements relating to the first derivative, the second derivative, the level, and/or the trigger count threshold have been met for each sample period. In some embodiments, the updating operation 208 includes at least one of a first requirement operation 208a, a second requirement operation 208b, a third requirement operation 208c, a fourth requirement operation 208d, and/or a fifth requirement operation 208e. The ventilator during updating operation 208 does not update the sample count until at least one of a first predetermined requirement, a second predetermined requirement, a third predetermined requirement, a fourth predetermined requirement, and a the fifth predetermined requirement are checked during the performance of operations 208a, 208b, 208c, 208d, and/or 208e.

In some embodiments, a first predetermined requirement is that a current triggering threshold has to be equivalent to the previous triggering threshold. As such, in these embodiments, the ventilator during the first requirement operation 208a of updating operation 208 compares the trigger count threshold selected for a current sample period to a previous trigger count threshold selected in a previous sample period. If the ventilator during the first requirement operation 208a determines that the current trigger count threshold is not equal to the previous trigger count threshold, the ventilator updates the sample count to zero. In some embodiments, if the ventilator during the first requirement operation 208a determines that the current trigger count threshold is equal to the previous trigger count threshold, the ventilator updates the sample count (n) to n+1. In alternative embodiments, if the ventilator during the first requirement operation 208a determines that the current trigger count threshold is equal to the previous trigger count threshold, the ventilator determines if another predetermined requirement has been met or checks another comparison result.

In some embodiments, a second predetermined requirement is that the first derivative (also referred to as the current first derivative) for the current sample period is less than the first derivative (also referred to as the previous first derivative) calculated for the previous sample period. As such, in these embodiments, the ventilator during the second requirement operation 208b of updating operation 208 compares the current first derivative to a previous first derivative. If the ventilator during the second requirement operation 208b determines that the current first derivative is equal to or greater than the previous first derivative, the ventilator updates the sample count to zero. In some embodiments, if the ventilator during the second requirement operation 208b determines that the current first derivative is less than the previous first derivative, the ventilator updates the sample count (n) to n+1. In alternative embodiments, if the ventilator during the second requirement operation 208b determines that the current derivative is less than the previous first derivative, the ventilator determines if another predetermined requirement has been met or checks another comparison result.

In some embodiments, the second predetermined requirement is additionally or alternatively that the second derivative (also referred to as the current second derivative) for the current sample period is less than the second derivative (also referred to as the previous second derivative) calculated for the previous sample period. As such, in these embodiments, the ventilator during a second requirement operation 208b of updating operation 208 compares the current second derivative to a previous second derivative. If the ventilator during the second requirement operation 208b determines that the current second derivative is equal to or greater than the previous second derivative, the ventilator updates the sample count to zero. In some embodiments, if the ventilator during the second requirement operation 208b determines that the current second derivative is less than the previous second derivative, the ventilator updates the sample count (n) to n+1. In alternative embodiments, if the ventilator during the second requirement operation 208b determines that the current derivative is less than the previous second derivative, the ventilator determines if another predetermined requirement has been met or checks another comparison result.

In some embodiments, a third predetermined requirement is that the array of maxima of the second derivative is less than an array threshold ($\psi$). As such, in these embodiments, the ventilator during a third requirement operation 208c of updating operation 208 compares the array of the second derivative to an array threshold. The array threshold may be determined by the ventilator or selected or input by the operator. If the ventilator during the third requirement operation 208c determines that the array of maxima of second derivative is more than or equal to the array threshold, the ventilator updates the sample count (n) to zero. In some embodiments, if the ventilator during the third requirement operation 208c determines that the array of maxima of the second derivative is less than the array threshold, the ventilator updates the sample count (n) to n+1. In alternative embodiments, if the ventilator during the third requirement operation 208c determines that the array of maxima of the second derivative is less than the array threshold, the ventilator checks one or more additional requirements before updating the sample count. The use of the array threshold as a predetermined requirement prevents or reduces auto triggering (also referred to as false triggering) caused by patient circuit vibration and/or noise. In alternative embodiments, the third requirement operation 208c utilizes an array of minima of the second derivative instead of the array of maxima.

In some embodiments, a fourth predetermined requirement is that the second derivative for the current sample period is less than the selected level. As such, in these embodiments, the ventilator during a fourth requirement operation 208d of updating operation 208 compares the current second derivative to the level selected for the same sample period. If the ventilator during the fourth requirement operation 208d determines that the current second derivative is greater than the selected level, the ventilator updates the sample count to zero. In some embodiments, if the ventilator during the fourth requirement operation 208d determines that the current second derivative is less than or equal to the level, the ventilator updates the sample count (n) to n+1. In alternative embodiments, if the ventilator during the fourth requirement operation 208d determines that the current derivative is less than or equal to the level, the ventilator determines if another predetermined requirement has been met or checks another comparison result.

In some embodiments, a fifth predetermined requirement is that a calculated rate of change for the second derivative for the current sample period is less than a rate threshold. As such, in these embodiments, the ventilator during a fifth requirement operation 208e of updating operation 208 compares a calculated rate of change for the second derivative to a rate threshold. In some embodiments, the ventilator during the fifth requirement operation 208e calculates a rate of change for the current second derivative. In other embodiments, the ventilator during monitoring operation 202 and/or calculating operation 204 calculates the rate of change for the current second derivative. In additional embodiments, the rate threshold is the Lipschitz constant. If the ventilator during the fifth requirement operation 208e determines that the current second derivative is equal to or greater than the rate threshold, the ventilator updates the sample count to zero. In some embodiments, if the ventilator during the fifth requirement operation 208e determines that the current second derivative is less than the rate threshold, the ventilator updates the sample count (n) to n+1. In alternative embodiments, if the ventilator during the fifth requirement operation 208e determines that the current derivative is less than the rate threshold, the ventilator determines if another predetermined requirement has been met or checks another comparison result.

In some embodiments, the ventilator during updating operation 208 requires that each of the first predetermined requirement, the second predetermined requirement, the third predetermined requirement, the fourth predetermined requirement, and the fifth predetermined requirement are met to update the sample count to n+1. In other embodiments, the ventilator during updating operation 208 requires that the fourth requirement be met to update the sample count to n+1. In some embodiments, the ventilator during updating operation 208 updates a sample count to zero if any one of the first predetermined requirement, the second predetermined requirement, the third predetermined requirement, the fourth predetermined requirement, and the fifth predetermined requirement are not met. In other embodiments, the ventilator during updating operation 208 updates the sample count to zero if fourth requirement is not met. The updating operations 208 may be performed by the inspiration module, processor, controller, pneumatic system, exhalation module, parameter module, sensors, derivative module threshold module and/or counter module of the ventilator.

Next, method 200 includes a comparing operation 210. During the comparing operation 210, the ventilator compares the updated sample count for the current sample period to the trigger count threshold for the current sample period. If the ventilator determines during the comparing operation 210 that the updated sample count is not equal to the trigger count threshold (also referred to herein as a second result), the ventilator performs monitoring operation 202 for the next sample period. If the ventilator determines during the comparing operation 210 that the updated sample count is equal to the trigger count threshold (also referred to herein as a first result), the ventilator performs triggering operation 212. The comparing operations 210 may be performed by the processor, controller, pneumatic system, and/or compare module of the ventilator.

As illustrated in FIG. 2, method 200 also includes a triggering operation 212. During triggering operation 212, the ventilator triggers inspiration. In other words, the ventilator during triggering operation 212 delivers an inspiration to the patient and ends exhalation. The inspiration provided to the patient may be determined by the ventilator and/or patient parameters. For example, the delivered inspiration may be based on a breath type or a ventilation mode, such as a proportional assist breath type or any other suitable spontaneously triggered breath type or mode. After the performance of the triggering operation 212, the ventilator updates the sample count to zero and then performs monitoring operation 202 for the next sample period. The triggering operations 212 may be performed by the inspiration module, processor, controller, pneumatic system, parameter module, exhalation module, sensors, and/or trigger module of the ventilator.

In other embodiments, method 200 includes a display operation. The ventilator during the display operation displays any suitable information for display on a ventilator. In one embodiment, the display operation displays at least one of a trigger count threshold, a sample count, a level, a rate threshold, a ratio threshold, the predetermined requirements, a physiological parameter, a graph or waveform of the physiological parameter, a detected patient trigger, a counted sample, and/or any other information known, received, or stored by the ventilator.

While method 200 is described with regards to triggering inspiration utilizing the DSCT mode, the same principles could be applied for cycling exhalation utilizing the DSCT mode by using different predetermined requirement and threshold values as would be known and understood by a person of skill in the art. For example, the DSCT mode detects cycling by detecting when the digital samples become almost equal and flat in their magnitude (on a plateau waveform) at the end of inhalation.

In some embodiments, a microprocessor-based ventilator that accesses a computer-readable medium having computer-executable instructions for performing the method of ventilating a patient with a medical ventilator is disclosed. These embodiments include performing or repeatedly performing based on stored instructions the operations disclosed in method 200 above and/or as illustrated in FIGS. 2, 3, 4, and/or 5. In further embodiments, method 200 is performed by the ventilator 100 described above and illustrated in FIG. 1. In some embodiments, the ventilator system includes: means for performing the steps or operations of method 200.

EXAMPLES

Example 1

Example 1 illustrates an embodiment of an algorithm utilized by method 200 or by the ventilator 100 to perform DSCT mode. The following list of equations and parameters are exemplary only and are not meant to be limiting.

The example algorithm employs the first and second derivatives ($\dot{X}$ and $\ddot{X}$) of the signal X (e.g., estimated patient effort) in real time, amplifies them by an amplification factor $K_{\dot{X}}$=50 and $K_{\ddot{X}}$=10 (respectively) and performs signal processing as described below. The triggering algorithm uses an extremum seeking subsystem which detects the minima and maxima of $\dot{X}$ and $\ddot{X}$ signals in real time. The algorithm keeps the last maximum found on the first derivative signal $\dot{X}_{max}$ and buffers the maxima found on the second derivative signal during exhalation phase. A flag is employed to show the final extremum point found on the second derivative is a minimum or maximum as shown in EQUATION #1 below:

$$(\ddot{X}_{Min})_{flag} = \begin{cases} 1 & \text{if the last } extremum \text{ found on the Second derivative is a Minimum} \\ 0 & \text{if the last } extremum \text{ found on the Second derivative is a Maximum} \end{cases} \quad \text{EQ \#1}$$

Furthermore, all the peaks of the second derivative signal $\ddot{X}_{Max}$ during patient respiratory signal observation are dynamically buffered in an array $D_{\ddot{X}_{Max}}$ as illustrated in the Equation #2 below:

$$D_{\ddot{X}_{Max}} = [\ddot{X}_{Max1}, \ddot{X}_{Max2}, \ldots] \quad \text{EQ\#2}$$

In other words, $D_{\ddot{X}_{Max}}$ is a vector that includes 3 arrays which are the last buffered maxima of the second derivative signal. The following inequality is the initial condition that must be satisfied to verify other triggering criteria as illustrated in Equation number #3 below:

$$\text{NetFlow} \leq 0.5 \times \text{Peak}_{NetFlow} \quad \text{EQ\#3}$$

where $\text{Peak}_{NetFlow}$ is the first peak found on the NetFlow ($q_N$) signal after it reaches 3 Lpm during exhalation phase. The net instantaneous flow of gas into the patient tubing system, $q_N$, is defined in Equation #4 as follows:

$$q_N = q_{insp} - q_E \quad \text{EQ\#4}$$

where $q_{insp}$ and $q_E$ are the raw flow reading of the inspiratory flow sensor, and the unfiltered value of the flow passing through the exhalation port. All flow readings are expressed in liters per second (lps). In some instances, a unit conversion is required to transform these flows from liters per minute (lpm) to lps, which is accomplished by dividing the lpm values by 60 to obtain flows expressed in lps.

Once the above condition is met, all the following parameters in the algorithm will be reset to their initial values as the following table and the algorithm starts verifying the other triggering conditions.

TABLE 1

Initial value of parameters in the algorithm for the DSCT Mode

| Parameter | Initial value |
|---|---|
| $\dot{X}_{max}$ | 1000 |
| $\ddot{X}_{max}$ | 1000 |
| $\ddot{X}_{min}$ | 0 |
| $D_{\ddot{X}_{Max}}$ | [0, 0, 0] |
| $(\ddot{X}_{Min})_{flag}$ | 0 |
| $\text{Peak}_{NetFlow}$ | −2000 |
| SampleCounter | 0 |

The last maximum found on the first derivative signal, the flag that shows whether the last maximum found on the second derivative signal was a Max or Min and the past extrema found on the second derivative signal will be used for signal/noise ratio estimation purposes. In the following algorithm, the inspiration occurs once the number of digital samples counted by a dynamic counter reaches a predefined value (SampleCountSize=N>0). Furthermore, the counter starts counting after the signal $\ddot{X}$ reaches a predefined sensitivity threshold (SampleCountStartLevel=L<0). The target sample size (N) and the sample counting starting level (L) dynamically alter inside the algorithm depending on the variation of the Signal/Noise ratio (S/R). The Signal/Noise ratio variation can be caused by several factors such as any thermo-dynamical changes that affect the fluid dynamics inside the patient tubing or any unwanted vibration of the patient circuit. The new method introduces a Signal/Noise ratio estimation algorithm. The output of this algorithm is a function of the signal's second derivative amplitude $\ddot{X}$, slope and the array of the previous maxima ($D_{\ddot{X}_{Max}}$) occurred since the above initial Net flow condition (Equation #3) is met during the exhalation phase of the previous breath. This functionality is introduces by the following function, Equation #5, as shown below:

$$\Gamma(\ddot{X}(i), \ddot{X}(i-1), D_{\ddot{X}max}, d_v) = \quad \text{EQ \#5}$$

$$\begin{cases} \text{if} & \ddot{X}(i) < \gamma < 0 \ \& \ \ddot{X}(i) - \ddot{X}(i-1) < 0 \ \& \\ & |\ddot{X}(i) - \ddot{X}(i-1)| < d_v \text{ then } S/N(i)_{flag} = 1 \\ \text{otherwise} & S/N(i)_{flag} = 0 \end{cases}$$

"i" is an index that represents the state of the digital sampled signal.

The SampleCountStartLevel ($L_1$, $L_2$), the SampleCountSize ($N_1$, $N_2$), and the boundaries on the maximum of the maxima of the $\ddot{X}$ i.e. ($\tau$, $\psi$) mapped to the five inspiration sensitivity scales are defined in the following table:

TABLE 2

Design parameter values mapped to the DSC triggering sensitivities

| Sensitivity Scales | $L_1$ | $L_2$ | $N_1$ | $N_2$ | $\tau$ | $\psi$ |
|---|---|---|---|---|---|---|
| The most Sensitive | −3 | −8 | 2 | 4 | 70 | 70 |
| More Sensitive | −4 | −9 | 2 | 4 | 60 | 60 |
| Default | −5 | −10 | 2 | 4 | 50 | 50 |
| Less Sensitive | −10 | −15 | 2 | 4 | 40 | 40 |
| The least Sensitive | −15 | −20 | 2 | 4 | 30 | 30 |

The amplification factors of the $\dot{X}$ and $\ddot{X}$ signals and the control design parameters are defined below in Table 3.

TABLE 3

Amplification gains and control design parameters

| | |
|---|---|
| $K_{\dot{X}}$ | 50 |
| $K_{\ddot{X}}$ | 10 |
| $d_v$ | 5 |
| $\gamma$ | −1 |
| $\lambda$ | 1 |

$\gamma$ is the upper bound on the magnitude of the current sample of the second derivative signal. This boundary is a control design parameter. $d_v$ is a constant bound which represents the modulus of uniform continuity or Lipschitz continuity characteristics of the second derivative function. The Lipschitz characteristic of a function shows how fast it can change. In other words, for every pair of points on the waveform of this signal, the absolute value of the slope of the line connecting them is no greater than a definite real number $d_v$.

The $d_v$ has been employed as a tuning design parameter in this algorithm to distinguish between noise and meaningful signal. The higher value $d_v$ has, the less likelihood is the sampled signal to be considered as noise. $S/N(i)_{Flag}$ is an index that shows if the estimated signal to noise ratio is big enough to characterize the triggering criteria. If the $S/N(i)_{Flag}=1$ (in other words the signal/noise ratio is big enough), the algorithm will proceed with more relaxed triggering criteria (lower NSampleCountSize and higher LSampleCountStartLevel). The lower value of the NSampleCountSize and higher LSampleCountStartLevel represent the closest instance to the beginning of the neural inspiration. If the $S/N(i)_{flag}=0$ (in other words the signal/noise ratio has not been considered not big enough) then algorithm proceeds with a rigid triggering criteria. However, the algorithm does not block triggering just because of this estimation; instead, the algorithm penalizes the triggering criteria by stiffening the triggering criteria (higher NSampleCountSize and lower LSampleCountStartLevel). These criteria dynamically change in the algorithm depending on the signal/noise ratio variation of the current sample S/N(i) and the amplitudes of the previous maximum points found on the second derivative signal. The target sample size (NSampleCountSize) will be restricted to a higher value (e.g. stiffer triggering condition) if the maximum of the previous maxima of the second derivative buffered in $D_{\ddot{X}_{Max}}$ overshoots a design threshold $\tau$. The higher the amplitude of these maxima, the more likely it is that the signal/noise ratio is smaller. This idea is expressed by the following condition, Equation #6, as shown below:

$$\text{Max}(D_{\ddot{X}_{Max}}) > \tau \Rightarrow N_{SampleCountSize} = N_2 \ N_2 > N_1 \qquad \text{EQ\#6}$$

Each time the signal/noise ratio criteria (e.g., $S/N(i)_{flag}$) changes, the "SampleCounter" which counts the samples will reset.

Once the triggering criteria are determined, the algorithm passes through another threshold criteria that evaluates the initiation criteria of the DSCT (Digital Sample Counting Trigger) algorithm. This function is presented below as Equation #7:

$$\Lambda(\ddot{X}(i), \ddot{X}(i-1)\ddot{X}_{Max}, L_{SampleCountStartLevel}) = \qquad \text{EQ \#7}$$
$$\begin{cases} \text{if} & \dot{X}_{Max} < \lambda > 0 \ \& \ \ddot{X}(i) < L \ \& \ \ddot{X}(i) - \\ & \ddot{X}(i-1) < 0 \text{ then } SampleCounter^+ \\ \text{otherwise} & \text{reset } SampleCounter \end{cases}$$

This functionality has been introduced by the second part of above mentioned pseudo code. $\lambda$ is the upper bound on the magnitude of the last maximum of the first derivative signal. This boundary is a control design parameter that verifies if the rate of change of the main signal (speed) is small enough and the fluctuations of the main signal are stabilized enough to verify the patient respiratory demand and start the algorithm. As it was mentioned earlier, L is the dynamic threshold (SampleCountStartLevel) that the SampleCounter starts counting after the signal $\ddot{X}$ reaches this level. If the slope of the current sample of the second derivative signal becomes positive, the SampleCounter will be reset to zero.

Once the initiation criteria of the algorithm are evaluated, the algorithm evaluates the compaction of the magnitudes of the digital signal samples. Once the initiation criteria of the algorithm are evaluated, the algorithm passes through another threshold that evaluates the compaction of the magnitudes of the digital signal samples. This function is expressed as Equation #8 below and has been introduced in the inner loop condition of the second part of the above mentioned pseudo code:

$$\Psi(N_{SampleCounter}, \ddot{X}_{Min}, D_{\ddot{X}_{Max}}, N_{SampleCountSize}) = \qquad \text{EQ \#8}$$
$$\begin{cases} \text{if} & SampleCounter = N+1 \ \& \ (\ddot{X}_{Min})_{flag} = 0 \ \& \\ & \text{Max(last three elements of } D_{\ddot{X}_{Max}}) < \\ & \Psi \text{ then } IE = \text{TRUE} \\ \text{otherwise} & IE = \text{FALSE} \end{cases}$$

$\psi$ is the upper bound on the magnitude of the last three maxima of the second derivative signal. This boundary is a control design parameter that reflects the desired limitation on the acceleration of the variations on the main signal ($\ddot{X}$) to be small enough, therefore, the fluctuations on this signal are stabilized enough to evaluate the compaction of the digital samples for a predetermined time interval.

The algorithm triggers a new breath if the number of samples counted in time interval $\Delta t$ reaches the obtained target sample size N+1 before the slope of the current sample of the second derivative signal becomes positive (i.e. before a new minimum is found on the second derivative signal). This is the final triggering criterion that evaluates how squeeze are the magnitudes of the digital samples of the second derivative signal in the time interval $\Delta t$ and determine breath delivery. The time interval $\Delta t$ is equal to the target sample size number N obtained in the signal/noise ratio estimation algorithm multiplied by the ventilator fixed sampling time period (T) as illustrated in Equation #9 below:

$$\Delta t = N \times T \qquad \text{EQ\#9}$$

The upper bound on the differences of the magnitudes of the samples is $d_v$, which represents the Lipschitz constant of the second derivative function in the design algorithm. This can be attributed to how fast a certain number of consecutive sampling points on the second derivative signal must change to be interpreted as the meaningful patient respiratory demand against noise. The more scattered are the magnitude of these samples, the less is the signal/noise ratio.

Once the above condition is met and the ventilator triggers a new breath, all the parameters in the above table will be reset to their initial values and the algorithm starts verifying the exhalation criteria.

Example 1 can be illustrated by the following pseudo code:

```
if Ẋ (i) < γ && Ẍ (i) < Ẍ (i - 1) && Ẍ (i) > Ẍ (i - 1) - d_v
    L = L_1 ;
    S / N (i)_Flag = 1 ;
    if S / N (i - 1)_Flag == 0 ,
        Counter = 0 ;
    end
    if Max (D_ẌMax) < τ
        N = N_1 ;
    else
        N = N_2 ;
    end
else
    L = L_2 ;
    N = N_2 ;
    S / N (i)_Flag = 0 ;
    if S / N (i - 1)_Flag == 1,
        Counter = 0 ;
    end
```

```
    end
    if Ẍ (i) > Ẍ (i − 1)
        Counter = 0 ;
    end
```

During every control cycle, the ventilator determines the subsequent value of the logical breath phase variable IE, according to the following rule:

IE(i)=(InspCondMe t(i) or !ExhCondMet (i))

and initial conditions:

IE(i≤0)=FALSE.

```
if Ẋ_max ≤ λ && Ẍ (i) < Ẍ (i − 1) && Ẍ (i) < L
    Counter = Counter + 1 ;
    if Counter > N && (Ẍ_Min )Flag == 0 && Max(last three elements
        of D_ẊMax ) < ψ
        && IE (i − 1) == FALSE && Current exhalation has lasted
        longer than 200 ms
            InspCondMe t (i) = TRUE ;
            Counter = 0 ;
    else
            InspCondMe t (i) = FALSE ;
    end
else
    InspCondMe t (i) = FALSE ;
end.
```

Example 2

Figure 6:
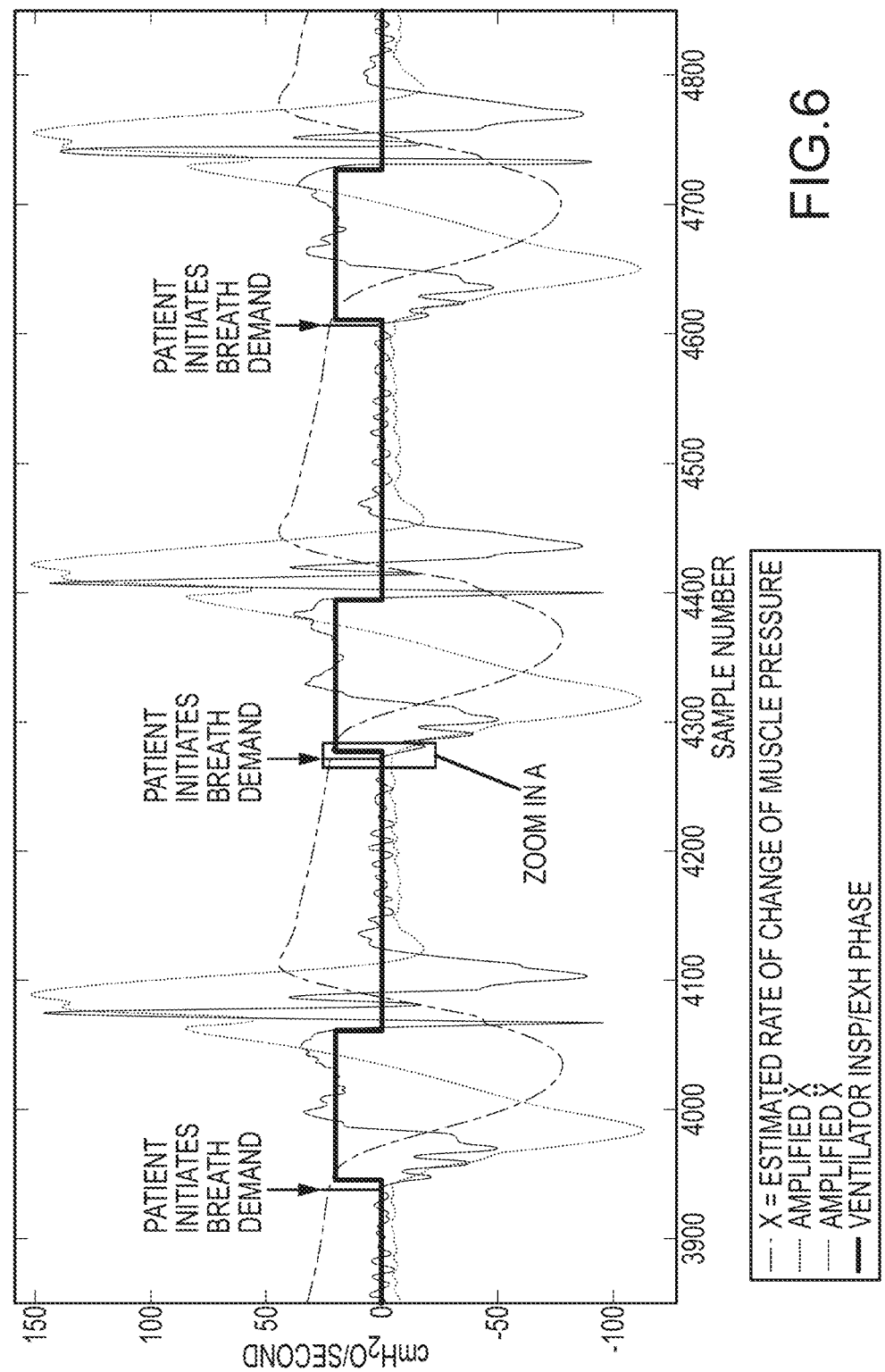
FIG. 6 illustrates an embodiment of a graph showing various signals related to estimated patient effort and phases of respiration by sample period for a patient being ventilated by a ventilator in a digital sample counting trigger mode.
Figure 7:
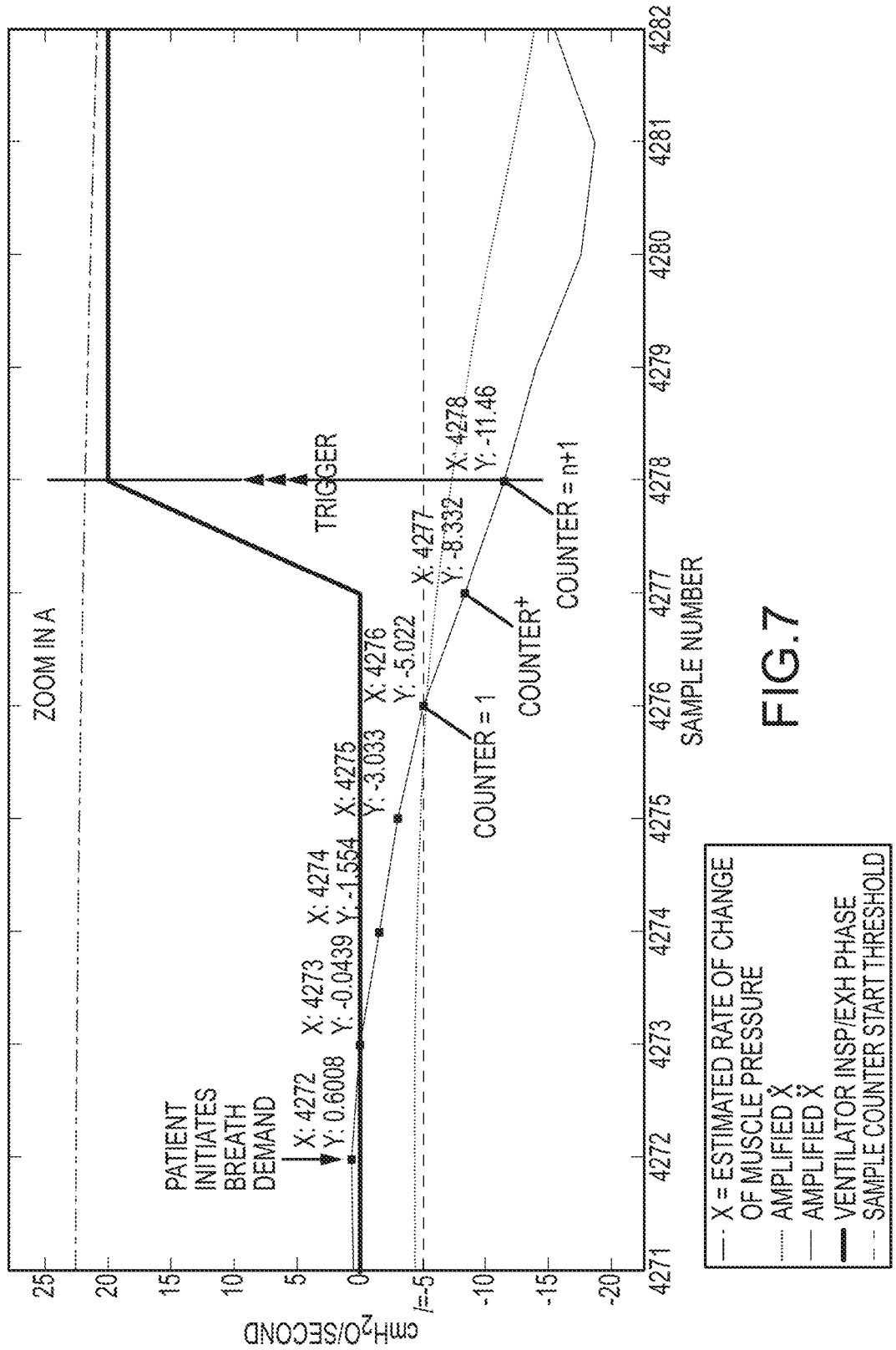
FIG. 7 illustrates a portion of the graph illustrated in FIG. 6.
Figure 11:
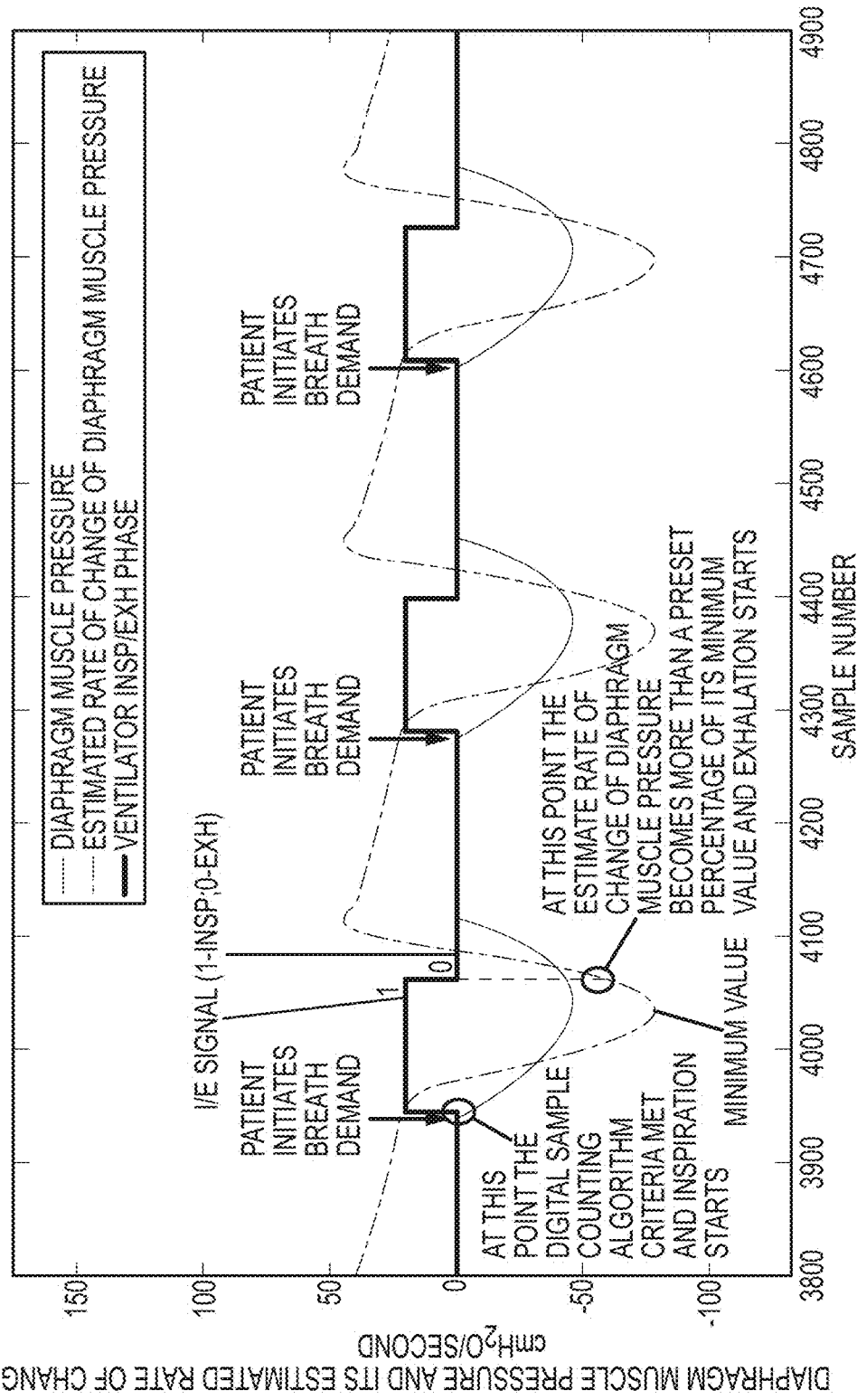
FIG. 11 illustrates an embodiment of a graph showing various signals related to estimated patient effort and phases of respiration by sample period for a patient being ventilated by a ventilator in a digital sample counting trigger mode.

FIGS. 6 and 11 illustrate an embodiment of a graph showing various signals related to estimated patient effort and phases of respiration by sample period for a patient being ventilated by a ventilator in a DSCT mode. FIG. 7 illustrates a portion of the graph illustrated in FIG. 6. FIG. 11 shows the muscle pressure signal generated by an active lung simulator lung and an estimated rate of change of the estimated patient effort (X) of the patient by sample period. FIG. 11 additionally illustrates the inspiratory and expiratory phases provided by the ventilator to the patient by sample period. As illustrated in FIG. 11, the estimated patient effort has some lag to reflect the exact derivative of muscle pressure signal because 1) the estimated patient effort is an estimation and it is not exact and 2) the estimation of the patient effort passes through different filters accounting for the time lag. However, if you look at the estimated patient effort within a smaller window (frame) at a given time period, the estimated patient effort's consecutive digital samples reflect the meticulous changes (up and downs) of patient respiratory demand (or actual patient effort) signal in real time regardless of the time lag or estimation error that existed in the estimated patient effort. This valuable information is transferred and magnified by the amplified first and second derivative of estimated patient effort.

FIG. 6 shows the waveform for an amplified first derivative of an estimated rate of change of muscle pressure a waveform of an amplified second derivative of the estimated rate of change of muscle pressure (Ẋ), and the estimated rate of change of the muscle pressure (X) of the patient by sample period. FIG. 6 also illustrates the inspiratory and expiratory phases provided by the ventilator to the patient by sample period. FIG. 7 additionally illustrates the level for each sample period shown as selected by the ventilator in a DSCT mode. Each sample period in this embodiment is 5 milliseconds (ms). FIG. 7 shows that the amplified second derivative of an estimated muscle pressure (Ẍ) started to decrease at sample number 4273, just one sample after a patient attempted to trigger inspiration. As shown by FIG. 7, the ventilator in the DSCT mode detected the patient trigger at sample number 4278, which is merely 30 ms (or six sample periods) after the patient attempted to trigger ventilation. Conventional triggering modes require around 300 ms or more to detect a patient trigger. As such, the DSCT mode has increased the ventilator response to a patient initiated to trigger to less than 70 ms and, in some instances, as fast as 30 ms. As such, the DSCT mode provides a significant advantage/improvement over previously utilized or conventional flow triggering modes. FIG. 7 further illustrates that the ventilator in the DSCT mode did not begin to count samples until the amplified second derivative of the estimated muscle pressure became less than the selected level of −5 cm of $H_2O$ per second at sample number 4276 (Ẍ=−5.022 $cmH_2O$/sec). Additionally, FIG. 7 illustrates that sample 4277 and 4278 were counted since each amplified second derivative of an estimated muscle pressure in each of these samples was less than the previous sample and below the selected level for that sample period. Further, FIG. 7 illustrates that the selected level −5 did not change from sample period 4272 through sample period 4278.

Example 3

Figure 8:
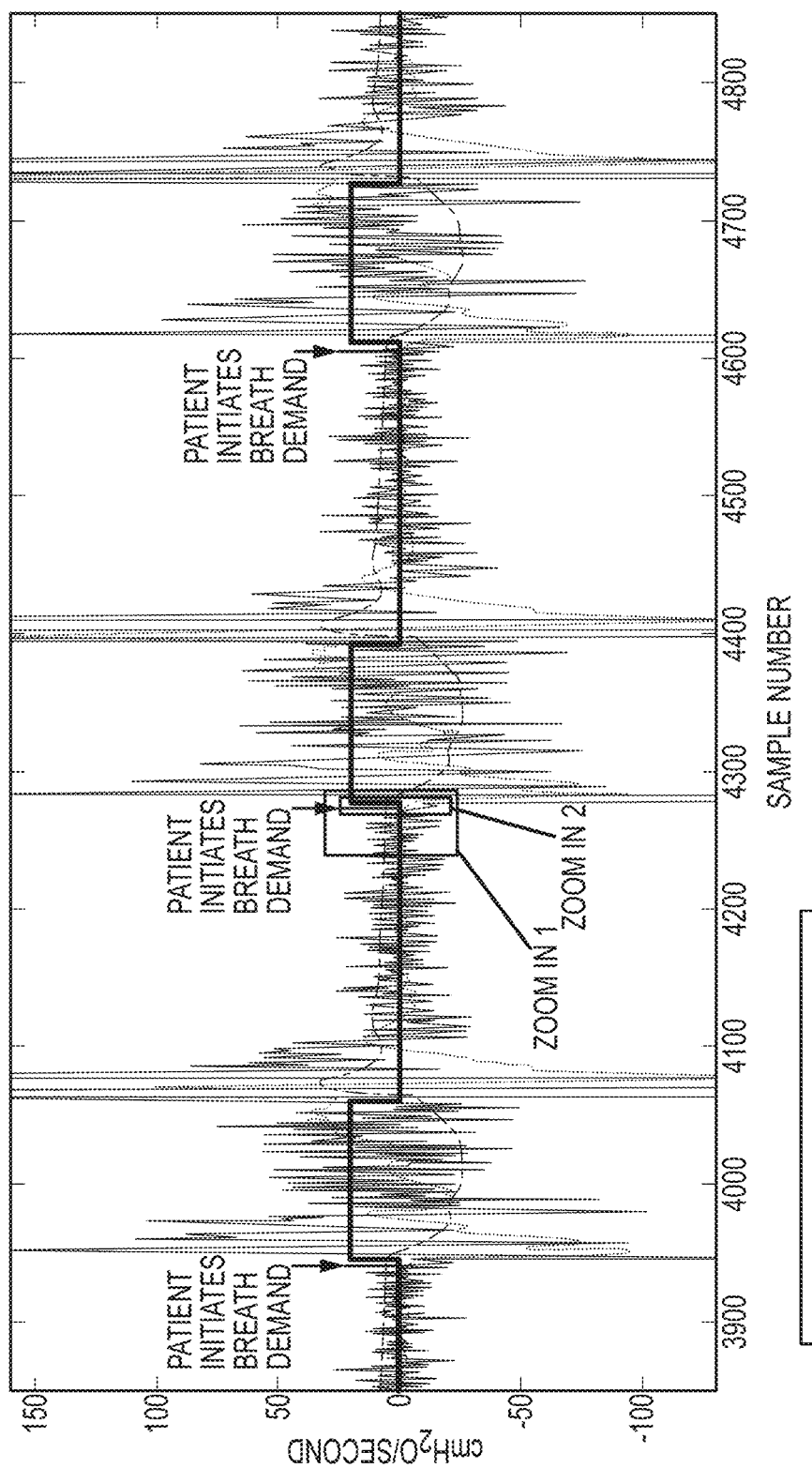
FIG. 8 illustrates an embodiment of a graph showing various signals related to net flow and phases of respiration by sample period for a patient being ventilated by a ventilator in a digital sample counting trigger mode.
Figure 9:
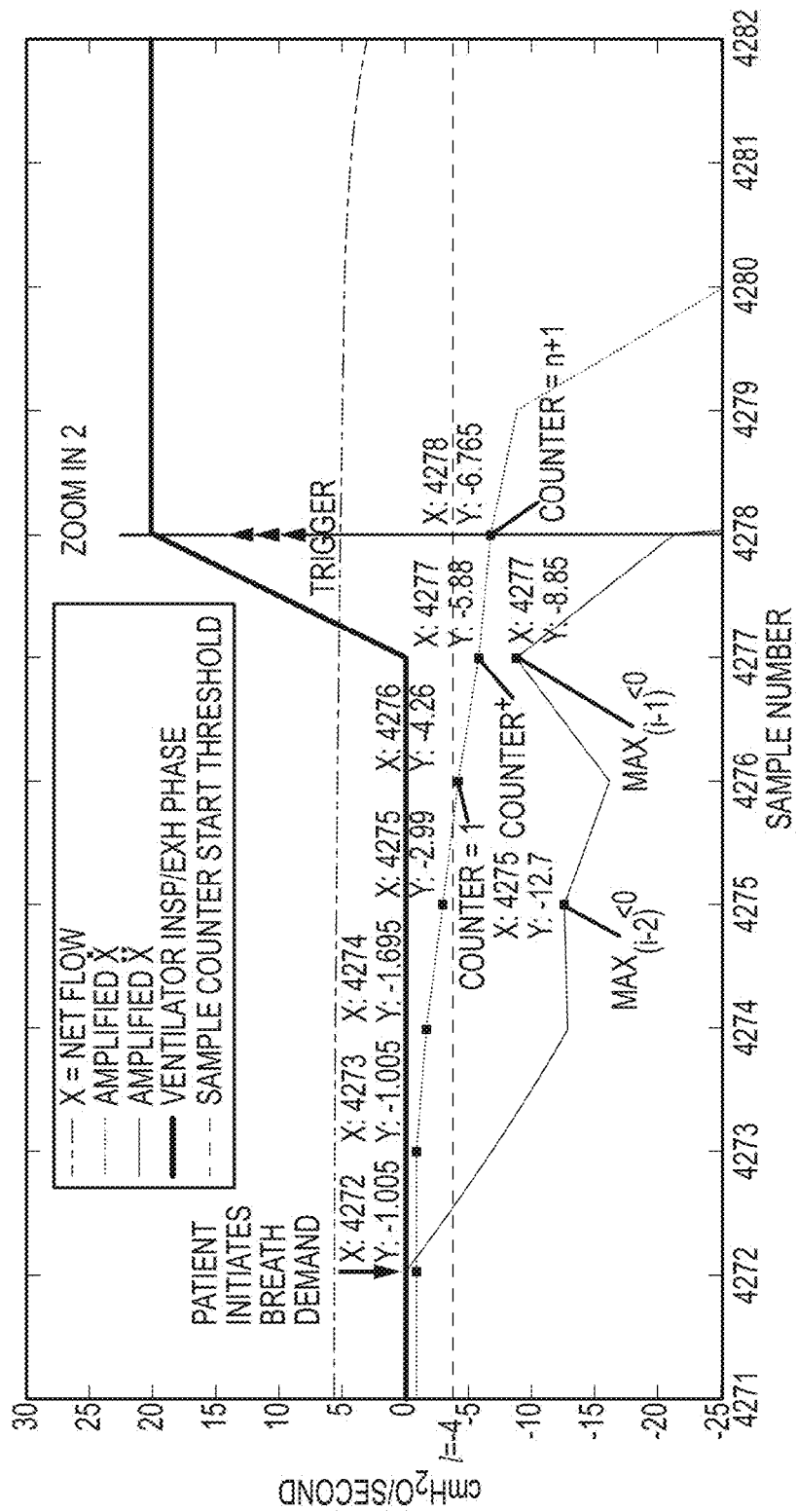
FIG. 9 illustrates a portion of the graph illustrated in FIG. 8.
Figure 12:
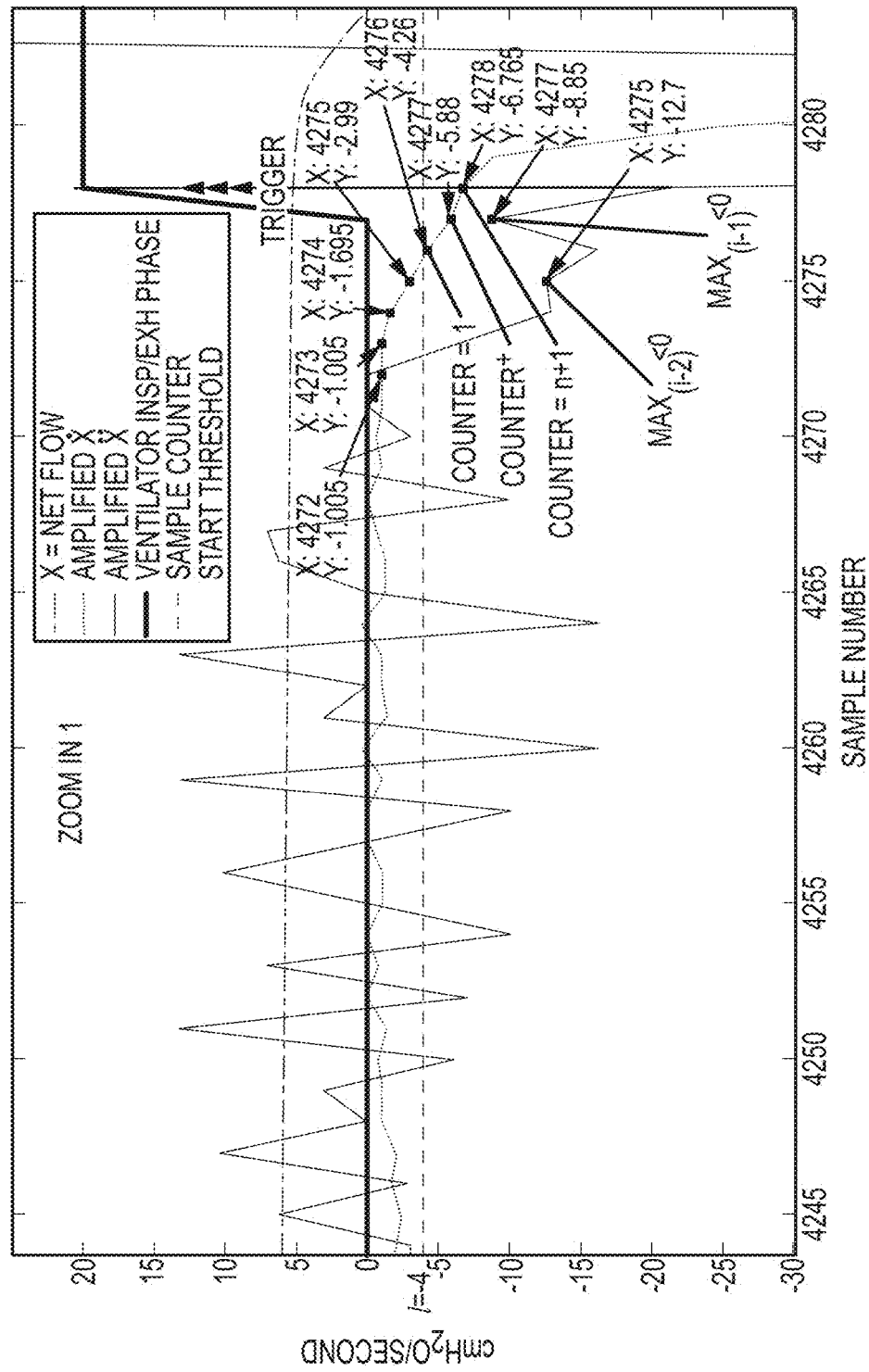
FIG. 12 illustrates a portion of the graph illustrated in FIG. 8.

FIG. 8 illustrates an embodiment of a graph showing various signals related to net flow and phases of respiration by sample period for a patient being ventilated by a ventilator in a DSCT mode. FIGS. 9 and 12 illustrate a portion of the graph illustrated in FIG. 8. FIG. 9 illustrates a zoomed in portion of the graph illustrated in FIG. 8 that is larger than the zoomed in portion illustrated in FIG. 12. FIG. 8 shows the waveform for an amplified first derivative of net flow (Ẋ), a waveform of an amplified second derivative of net flow (Ẍ), and the net flow (X) of the patient by sample period. FIG. 8 additionally illustrates the inspiratory and expiratory phases provided by the ventilator to the patient by sample period. FIGS. 9 and 12 additionally illustrate the level for each sample period shown as selected by the ventilator in a DSCT mode for each sample period. Each sample period in this embodiment is 5 ms. FIG. 9 shows that the amplified second derivative of net flow (Ẍ) started to decrease at sample number 4273, just one sample after a patient attempted to trigger inspiration. As shown by FIG. 9, the ventilator in the DSCT mode detected the patient trigger at sample number 4278, which is merely 30 ms (or 6 sample periods) after the patient attempted to trigger ventilation. Conventional triggering modes require around 300 ms or more to detected patient trigger. As such, the DSCT mode has increased the ventilator response to a patient initiated to trigger to less than 70 ms and, in some instances, as fast as 30 ms as illustrated in FIG. 9. As such, the DSCT mode provides a significant advantage/improvement over previously utilized or conventional flow triggering modes. FIG. 9 further illustrates that the ventilator in the DSCT mode did not begin to count samples until the amplified second derivative of the net flow became less than the selected level of −4 liters (the more sensitivity level shown in Table 2 above) per second at sample number 4276 (Ẍ=−4.26 l/sec). Additionally, FIG. 9 illustrates that sample 4277 and 4278 were counted since each amplified second derivative of net flow in each of these samples was less than the previous sample and below the selected level for that sample period. Further, FIG. 9 illustrates that the selected level −4 l/sec did not change from sample period 4271 through sample period 4278.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present disclosure.

What is claimed is:

1. A method for ventilating a patient with a ventilator, comprising:
    monitoring a physiological parameter of the patient based on one or more received sensor measurements;
    calculating a first derivative of the physiological parameter for a first sample period;
    selecting a first trigger count threshold;
    selecting a first level for the first derivative;
    updating a sample count to form a first updated sample count for the first sample period based on first comparison results from at least one of the following:
        comparing the first trigger count threshold to a previous trigger count threshold selected in a previous sample period,
        comparing the first derivative to a previous first derivative calculated for the previous sample period, and
        comparing the first derivative to the first level,
    comparing the first updated sample count to the first trigger count threshold; and
    triggering inspiration based on a first result of the comparing of the first updated sample count to the first trigger count threshold.

2. The method of claim 1, wherein the first result is that the first updated sample count is equal to the first trigger count threshold.

3. The method of claim 1, wherein the comparing of the first updated sample count to the first trigger count threshold has a second result, wherein the second result is that the first updated sample count is not equal to the first trigger count threshold.

4. The method of claim 3, further comprising:
    calculating a next first derivative of the physiological parameter for a second sample period;
    selecting a second trigger count threshold and a second level for the first derivative;
    updating the first updated sample count to form a second updated sample count for the second sample period based on second comparison results from at least one of the following:
        comparing the second trigger count threshold to the first trigger count threshold;
        comparing the next first derivative to the first derivative for the first sample period, and
        comparing the first derivative to the second level;
    comparing the second updated sample count to the second trigger count threshold;
    determining that the second updated sample count is equal to the second trigger count threshold based on the comparison of the second updated sample count to the second trigger count threshold; and
    triggering inspiration based on the determining that the second updated sample count is equal to the second trigger count threshold.

5. The method of claim 1, wherein the first derivative is amplified.

6. The method of claim 1, wherein the first trigger count threshold is selected from a count of 2 or 4 passing samples.

7. The method of claim 1, wherein the first level is selected from one of the following groups:
    −3 cm of $H_2O$ per second and −8 cm of $H_2O$ per second;
    −4 cm of $H_2O$ per second and −9 cm of $H_2O$ per second;
    −5 cm of $H_2O$ per second and −10 cm of $H_2O$ per second;
    −10 cm of $H_2O$ per second and −15 cm of $H_2O$ per second; and
    −15 cm of $H_2O$ per second and −20 cm of $H_2O$ per second.

8. The method of claim 1, wherein the selecting the first trigger count threshold and the first level is based on the first derivative and comprises:
    determining a signal to noise ratio of the first derivative; and
    comparing the signal to noise ratio of the first derivative to a ratio threshold.

9. The method of claim 8, wherein the selecting the first trigger count threshold and the first level is based on the first derivative and further comprises:
    determining that the signal to noise ratio for the first derivative is greater than the ratio threshold based on the comparing the signal to noise ratio for the first derivative to the ratio threshold; and
    selecting a small trigger count threshold for the first trigger count threshold and selecting a large level for the first level based on the determining that the signal to noise ratio for the first derivative is greater than the ratio threshold.

10. The method of claim 8, wherein the selecting the first trigger count threshold and the first level is based on the first derivative and further comprises:
    determining that the signal to noise ratio for the first derivative is less than or equal to the ratio threshold based on the comparing the signal to noise ratio for the first derivative to the ratio threshold; and
    selecting a large trigger count threshold for the first trigger count threshold and selecting a small level for the first level based on the determining that the signal to noise ratio for the first derivative is less than or equal to the ratio threshold.

11. The method of claim 1, wherein the updating the sample count for the first sample period further comprises:
    determining that the first trigger count threshold is equal to the previous trigger count threshold based on the comparing of the first trigger count threshold to the previous trigger count threshold;

determining that the first derivative is less than the previous first derivative calculated for the previous sample period based on the comparing the first derivative to the previous first derivative calculated for the previous sample period;

determining that the first derivative is less than or equal to the first level based on the comparing of the first derivative to the first level; and updating a previous sample count by +1 passing samples to form the first updated sample count.

12. The method of claim 1, wherein the updating the sample count for the first sample period further comprises at least one of the following:

determining that the first trigger count threshold is not equal to the previous trigger count threshold based on the comparing of the first trigger count threshold to the previous trigger count threshold, determining that the first derivative is equal to or more than the previous first derivative based on the comparing of the first derivative to the previous first derivative and, determining that the first derivative is more than the first level based on the comparing of the first derivative to the first level, and wherein the updating the sample count for the first sample period further comprises setting the first updated sample count to zero passing samples.

13. The method of claim 1, wherein the physiological parameter is an estimated patient effort.

14. The method of claim 1, wherein the physiological parameter is one of the following: a direct measurement of patient effort, a pressure, a flow, a net flow, a rate of change of flow, a rate of change of pressure, an estimated pressure, or an estimated flow.

15. A ventilator system comprising:

a pressure generating system that generates a flow of breathing gas;

one or more sensors operatively coupled to at least one of the pressure generating system, a patient, and a ventilation tubing system that delivers the flow of breathing gas from the pressure generating system to the patient, wherein the one or more sensors generate sensor output for each sample period;

a parameter module that monitors a physiological parameter from the sensor output for each sample period;

a derivative module that calculates a first derivative for the physiological parameter for each sample period;

a threshold module that selects a trigger count threshold and a level for the first derivative;

a counter module that updates a sample count based at least on the first derivative and the trigger count threshold for each sample period to form an updated sample count;

a compare module that compares a selected trigger count threshold to the updated sample count for a same sample period; and a trigger module that triggers inspiration based on a receipt of a first result from the compare module.

16. The ventilator system of claim 15, wherein the counter module determines that the trigger count threshold is equal to a previous trigger count threshold, wherein the counter module determines that the first derivative is less than a previous first derivative, wherein the counter module determines that the first derivative is less than or equal to the level, wherein the counter module updates the sample count by 1 passing sample to form the updated sample count, wherein the compare module determines that the updated sample count is equal to the selected trigger count threshold for the same sample period, and wherein the compare module sends the first result to the trigger module based on a determination that the updated sample count is equal to the selected trigger count threshold for the same sample period.

17. The ventilator system of claim 15, wherein the counter module determines at least one of the following comparison results:

the trigger count threshold is not equal to a previous trigger count threshold, the first derivative is equal to or more than a previous first derivative, the first derivative is more than the level, and wherein the counter module updates the sample count to zero passing samples to form the updated sample count, wherein the compare module determines that the updated sample count is not equal to the selected trigger count threshold for the same sample period, wherein the compare module sends a second result to the trigger module based on a determination that the updated sample count is not equal to the selected trigger count threshold for the same sample period, and wherein the trigger module does not trigger inspiration based on a receipt of the second result from the compare module.

18. The ventilator system of claim 15, wherein the physiological parameter is an estimated patient effort.

19. The ventilator system of claim 15, wherein the threshold module determines a signal to noise ratio for the first derivative for each sample period and compares the signal to noise ratio to a ratio threshold to select the trigger count threshold and the level for each sample period.

20. A computer-readable medium having computer-executable instructions for performing a method of ventilating a patient with a ventilator, the instructions comprising:

monitor an estimated patient effort of the patient based on received sensor measurements;

calculate a first derivative of the estimated patient effort for a sample period;

select a trigger count threshold and a level for the first derivative;

update a sample count to form an updated sample count for the first sample period based on a comparison result from comparing the first derivative to the level;

compare the updated sample count to the trigger count threshold; and trigger inspiration in response to the updated sample count meeting the trigger count threshold based on the comparing.

* * * * *